US012788360B2

(12) United States Patent
Horiuchi et al.

(10) Patent No.: US 12,788,360 B2
(45) Date of Patent: Nov. 10, 2026

(54) CONTROL APPARATUS, IMAGING SYSTEM, CONTROL METHOD, AND CONTROL PROGRAM

(71) Applicant: FUJIFILM Corporation, Tokyo (JP)

(72) Inventors: Hisatsugu Horiuchi, Kanagawa (JP); Koji Shimomura, Kanagawa (JP); Keiji Tsubota, Kanagawa (JP); Takeyasu Kobayashi, Kanagawa (JP); Sayaka Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 225 days.

(21) Appl. No.: 18/595,361

(22) Filed: Mar. 4, 2024

(65) Prior Publication Data

US 2024/0299001 A1 Sep. 12, 2024

(30) Foreign Application Priority Data

Mar. 10, 2023 (JP) ................................ 2023-038159

(51) Int. Cl.
*A61B 8/08* (2006.01)
*A61B 8/00* (2006.01)

(52) U.S. Cl.
CPC ............ *A61B 8/0825* (2013.01); *A61B 8/403* (2013.01); *A61B 8/4263* (2013.01); *A61B 8/461* (2013.01); *A61B 8/54* (2013.01)

(58) Field of Classification Search
CPC ....... A61B 6/4417; A61B 6/463; A61B 6/502; A61B 6/5264; A61B 8/0825; A61B 8/403; A61B 8/4263; A61B 8/461; A61B 8/54
See application file for complete search history.

(56) References Cited

U.S. PATENT DOCUMENTS

2010/0030078 A1* 2/2010 Mikami ............... A61B 6/4417 600/443
2017/0281131 A1 10/2017 Sendai

FOREIGN PATENT DOCUMENTS

JP 2010162058 A * 7/2010
JP 2017-176509 A 10/2017

OTHER PUBLICATIONS

Translated Hisayuki (Year: 2010).*

* cited by examiner

*Primary Examiner* — Brooke Lyn Klein
(74) *Attorney, Agent, or Firm* — Studebaker Brackett PLLC

(57) ABSTRACT

A control apparatus including: at least one processor, wherein the processor is configured to: acquire, in an order of time, for an ultrasound unit that captures an ultrasound image of a breast put into a compressed state by a compression member, is disposed on an upper surface side of the compression member opposite to a contact surface with the breast, and has an in-plane position in a plane direction of an upper surface and a height from the upper surface, which are changeable, height information indicating the height from the upper surface; determine whether or not the height indicated by the height information satisfies a predetermined condition; and specify, in a case in which an affirmative determination is made, a first position that is the in-plane position of the ultrasound unit in a predetermined period including a point in time at which the predetermined condition is satisfied.

8 Claims, 14 Drawing Sheets

CONTROL APPARATUS, IMAGING SYSTEM, CONTROL METHOD, AND CONTROL PROGRAM

CROSS-REFERENCE TO RELATED APPLICATIONS

This application claims priority from Japanese Application No. 2023-038159, filed on Mar. 10, 2023, the entire disclosure of which is incorporated herein by reference.

BACKGROUND

Technical Field

The present disclosure relates to a control apparatus, an imaging system, a control method, and a control program.

Related Art

In the related art, a mammography apparatus that captures a radiation image of a breast is known. In addition, in the terms of improving the detection accuracy of a lesion and improving the efficiency of an examination, an apparatus that can capture an ultrasound image of a breast in addition to a radiation image is proposed. For example, JP2017-176509A discloses an apparatus that captures a radiation image and an ultrasound image of a breast put into a compressed state by a compression member. In the apparatus described in JP2017-176509A, an ultrasound probe is moved along an upper surface (surface opposite to a surface on which the breast of an examinee is disposed) of the compression member.

In recent years, as in the technique described in JP2017-176509A, there is a need for a technique that can further support ultrasound imaging in the apparatus that captures the radiation image and the ultrasound image of the breast put into the compressed state by the compression member. For example, it is desired to reduce a compression time of the breast by reducing a time required for ultrasound imaging and to reduce the pain of the examinee as much as possible. In addition, for example, even in a case in which ultrasound imaging of the breast is performed via the compression member, it is desired to ensure a quality (resolution or the like) of the obtained ultrasound image.

SUMMARY

The present disclosure provides a control apparatus, an imaging system, a control method, and a control program that can acquire an in-plane position in a case in which an ultrasound unit is located at a height under a predetermined condition.

A first aspect of the present disclosure relates to a control apparatus comprising: at least one processor, in which the processor acquires, in an order of time, for an ultrasound unit that captures an ultrasound image of a breast put into a compressed state by a compression member, is disposed on an upper surface side of the compression member opposite to a contact surface with the breast, and has an in-plane position in a plane direction of an upper surface and a height from the upper surface, which are changeable, height information indicating the height from the upper surface, determines whether or not the height indicated by the height information satisfies a predetermined condition, and specifies, in a case in which it is determined that the height indicated by the height information satisfies the condition, a first position that is the in-plane position of the ultrasound unit in a predetermined period including a point in time at which the condition is satisfied.

In the first aspect, the processor may acquire a radiation image of the breast put into the compressed state by the compression member, may associate coordinates of the radiation image with the in-plane position, and may specify first coordinates of the radiation image corresponding to the specified first position.

In the first aspect, the processor may perform control of storing the radiation image and the first coordinates in a storage unit in association with each other.

In the first aspect, the processor may perform control of displaying, on a display, a first marker indicating the specified first coordinates in a state of being superimposed on the radiation image.

In the first aspect, the processor may specify, in a case in which it is determined that the height indicated by the height information does not satisfy the condition, a second position that is the in-plane position of the ultrasound unit in a predetermined period including a point in time at which the condition is not satisfied, may specify second coordinates of the radiation image corresponding to the specified second position, and may perform control of displaying, on the display, a second marker that indicates the specified second coordinates and has a different form from the first marker in a state of being superimposed on the radiation image.

In the first aspect, the processor may determine whether or not a temporal change amount of the height of the ultrasound unit from the upper surface in the predetermined period is equal to or greater than a predetermined threshold value, as the condition.

In the first aspect, the processor may determine whether or not an absolute value of the height of the ultrasound unit from the upper surface is smaller than a predetermined threshold value, as the condition.

In the first aspect, the processor may specify, in a case in which it is determined that the height indicated by the height information satisfies the condition, an angle of the ultrasound unit with respect to the upper surface in the predetermined period including the point in time at which the condition is satisfied, in addition to the first position.

A second aspect of the present disclosure relates to an imaging system comprising: the control apparatus according to the first aspect; and an imaging apparatus, in which the imaging apparatus includes a compression member that puts a breast into a compressed state between the compression member and an imaging table, a radiation source that irradiates the breast put into the compressed state by the compression member with radiation, an ultrasound unit that captures an ultrasound image of the breast put into the compressed state by the compression member, is disposed on an upper surface side of the compression member opposite to a contact surface with the breast, and has an in-plane position in a plane direction of an upper surface and a height from the upper surface, which are changeable, a first sensor that detects the height of the ultrasound unit from the upper surface, and a second sensor that detects the in-plane position of the ultrasound unit.

In the second aspect, the imaging apparatus may further include a first drive mechanism that moves the ultrasound unit between at least two states of an approach state in which the ultrasound unit approaches the upper surface, and a separation state in which the ultrasound unit is separated from the upper surface as compared to the approach state, and a second drive mechanism that moves the ultrasound unit put into the separation state by the first drive mechanism in the plane direction of the upper surface.

A third aspect of the present disclosure relates to a control method comprising: acquiring, in an order of time, for an ultrasound unit that captures an ultrasound image of a breast put into a compressed state by a compression member, is disposed on an upper surface side of the compression member opposite to a contact surface with the breast, and has an in-plane position in a plane direction of an upper surface and a height from the upper surface, which are changeable, height information indicating the height from the upper surface; determining whether or not the height indicated by the height information satisfies a predetermined condition; and specifying, in a case in which it is determined that the height indicated by the height information satisfies the condition, a first position that is the in-plane position of the ultrasound unit in a predetermined period including a point in time at which the condition is satisfied.

A fourth aspect of the present disclosure relates to a control program for causing a computer to execute a process comprising: acquiring, in an order of time, for an ultrasound unit that captures an ultrasound image of a breast put into a compressed state by a compression member, is disposed on an upper surface side of the compression member opposite to a contact surface with the breast, and has an in-plane position in a plane direction of an upper surface and a height from the upper surface, which are changeable, height information indicating the height from the upper surface; determining whether or not the height indicated by the height information satisfies a predetermined condition; and specifying, in a case in which it is determined that the height indicated by the height information satisfies the condition, a first position that is the in-plane position of the ultrasound unit in a predetermined period including a point in time at which the condition is satisfied.

According to the aspects described above, in the control apparatus, the imaging system, the control method, and the control program according to the present disclosure, it is possible to acquire the in-plane position in a case in which the ultrasound unit is located at the height satisfying the predetermined condition.

DETAILED DESCRIPTION

Hereinafter, a description of embodiments of the present disclosure will be made with reference to the accompanying drawings.

First Embodiment

Figure 1:
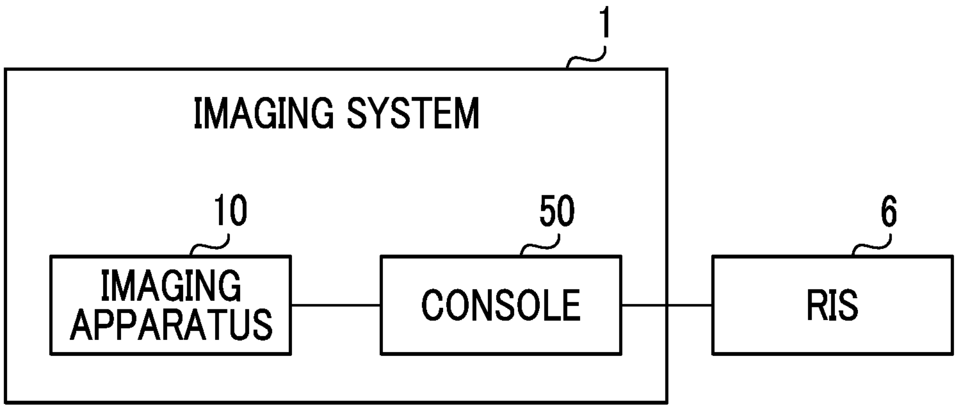
FIG. 1 is a view showing an example of a schematic configuration of an imaging system.

First, a description of a configuration of an imaging system 1 will be made with reference to FIG. 1. FIG. 1 is a view showing an example of a schematic configuration of the imaging system 1. As shown in FIG. 1, the imaging system 1 comprises an imaging apparatus 10 and a console 50. The imaging apparatus 10 and the console 50, and the console 50 and an external radiology information system (RIS) 6 are configured to be connected to each other via a wired or wireless network.

In the imaging system 1, the console 50 acquires an imaging order or the like from the RIS 6, and controls the imaging apparatus 10 in accordance with the imaging order, an instruction from the user, and the like. The imaging apparatus 10 acquires a radiation image and an ultrasound image of a breast of an examinee put into a compressed state by a compression member 40 as a subject. The console 50 is an example of a control apparatus according to the present disclosure.

Figure 2:
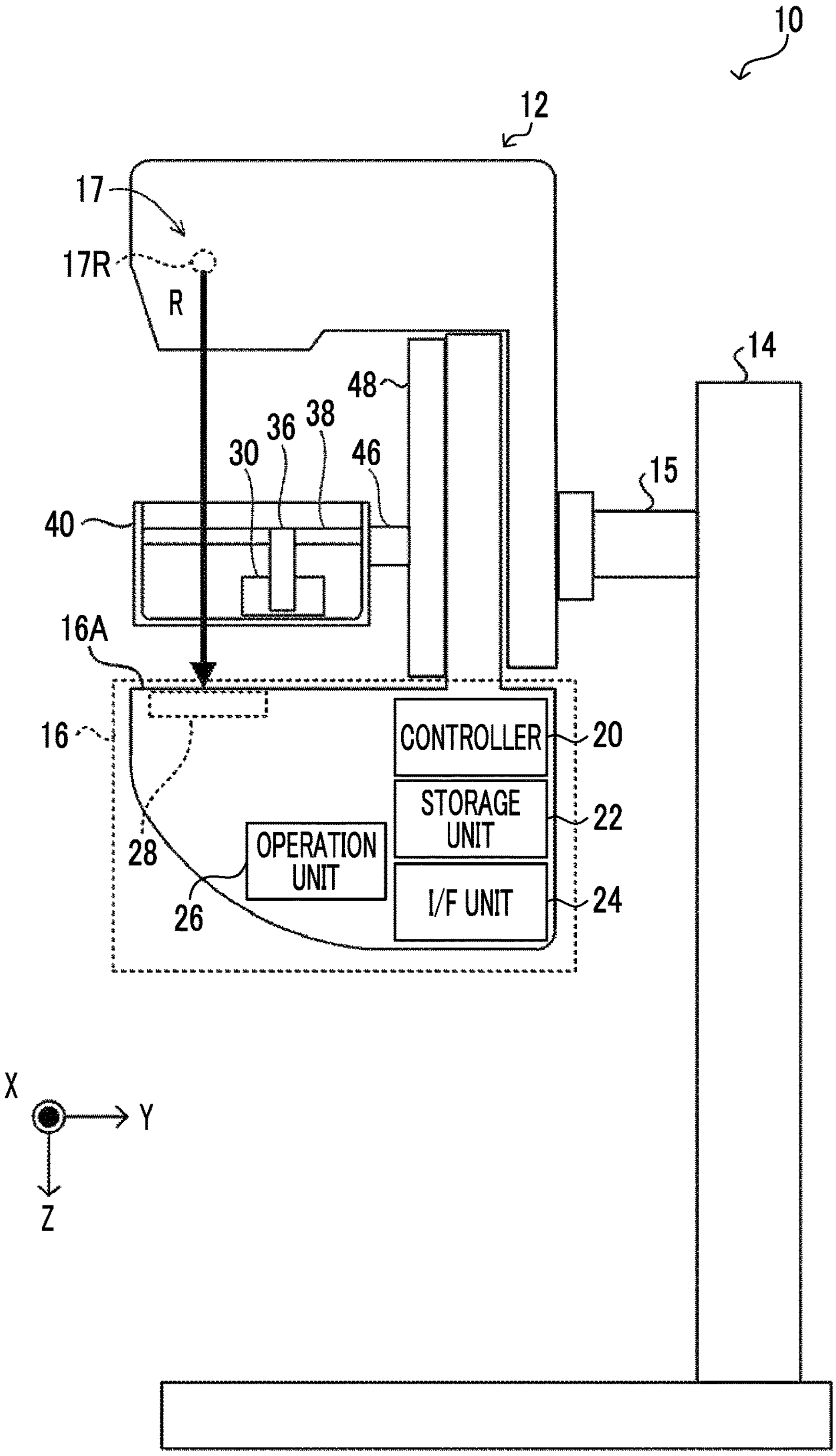
FIG. 2 is a side view showing an example of an appearance of an imaging apparatus.

Next, a description of a schematic configuration of the imaging apparatus 10 will be made with reference to FIG. 2. FIG. 2 is a side view showing an example of an appearance of the imaging apparatus 10, and is a view in a case in which the imaging apparatus 10 is viewed from a right side of the examinee. As shown in FIG. 2, the imaging apparatus 10 comprises a radiation source 17R, a radiation detector 28, an imaging table 16 disposed between the radiation source 17R and the radiation detector 28, and the compression member 40 that compresses the breast between the compression member 40 and the imaging table 16. In the imaging apparatus 10, a user, such as a doctor or a technician, positions the breast of the examinee on an imaging surface 16A of the imaging table 16.

The imaging apparatus 10 comprises an arm part 12, a base 14, and a shaft part 15. The arm part 12 is held to be movable in an up-down direction (Z direction) by the base 14. The shaft part 15 connects the arm part 12 to the base 14. The arm part 12 is relatively rotatable with respect to the base 14 with the shaft part 15 as a rotation axis. In addition, the arm part 12 may be relatively rotatable with respect to the base 14 with the shaft part 15 as the rotation axis separately between an upper part comprising a radiation emitting unit 17 and a lower part comprising the imaging table 16.

The arm part 12 comprises the radiation emitting unit 17 and the imaging table 16. The radiation emitting unit 17 comprises the radiation source 17R, and is configured to change an irradiation field of radiation (for example, X-rays) emitted from the radiation source 17R. For example, the change of the irradiation field may be performed by the user operating an operation unit 26, or may be performed by a controller 20 in accordance with a type of the attached compression member 40. The radiation source 17R irradiates the breast put into the compressed state by the compression member 40 with radiation R.

The imaging table 16 comprises the controller 20, a storage unit 22, an interface (I/F) unit 24, the operation unit 26, and the radiation detector 28. The controller 20 controls an overall operation of the imaging apparatus 10 in accordance with the control of the console 50. The controller 20 comprises a central processing unit (CPU), a read only memory (ROM), a random access memory (RAM), and the like (none shown). The ROM stores in advance various programs including a program executed by the CPU for performing the control related to the acquisition of the radiation image and the ultrasound image. The RAM transitorily stores various data.

Data of the radiation image and the ultrasound image, various types of other information, and the like are stored in the storage unit 22. The storage unit 22 is realized by, for example, a storage medium, such as a hard disk drive (HDD), a solid state drive (SSD), and a flash memory.

The I/F unit 24 performs communication of various types of information with the console 50 by wired or wireless communication. Specifically, the I/F unit 24 receives information related to the control of the imaging apparatus 10 from the console 50. Further, the I/F unit 24 transmits the data of the radiation image and the ultrasound image to the console 50.

The operation unit 26 is a part that is provided on the imaging table 16 or the like and can be operated by the user with a hand, a foot, or the like, and is, for example, a switch, a button, or a touch panel. For example, the operation unit 26 may receive a voice input from the user.

The radiation detector 28 is disposed in the imaging table 16, detects the radiation R transmitted through the breast and the imaging table 16, generates the radiation image based on the detected radiation R, and outputs image data indicating the generated radiation image. It should be noted that a type of the radiation detector 28 is not particularly limited and may be, for example, an indirect conversion type radiation detector that converts the radiation R into light and converts the converted light into a charge, or a direct conversion type radiation detector that directly converts the radiation R into a charge.

A compression unit 48 is connected to the arm part 12. A support part 46 that supports the compression member 40 is attachably and detachably attached to the compression unit 48. The support part 46 (compression member 40) is moved in the up-down direction (Z direction) by a driving unit (not shown) provided in the compression unit 48.

The compression member 40 is used to put the breast disposed on the imaging surface 16A into the compressed state. Specifically, the compression member 40 is disposed between the radiation source 17R and the imaging table 16 and interposes the breast between the compression member 40 and the imaging surface 16A of the imaging table 16 to put the breast into the compressed state. The compression member 40 includes a bottom part 43 formed to be substantially flat and surrounded by a wall part 44 having a substantially uniform height, and has a cross section shape formed in a recess shape. It is preferable that the bottom part 43 and the wall part 44 are formed of an optically transparent or translucent material in order to perform positioning and check of the compressed state in the compression of the breast. In addition, it is preferable that the bottom part 43 and the wall part 44 are formed of a material excellent in a transmittance of the radiation R and the ultrasound. In addition, it is preferable that the bottom part 43 and the wall part 44 are formed of, for example, a material excellent in strength, such as drop strength and compression strength.

As such a material, for example, resin, such as polymethylpentene (PMP), polycarbonate (PC), acryl, polypropylene (PP), and polyethylene terephthalate (PET), can be used. In particular, in the polymethylpentene, an acoustic impedance, which affects the transmittance and the reflectivity of the ultrasound, is closer to an acoustic impedance of a human body (breast) than other materials, and a proportion of the noise on the ultrasound image can be decreased. Therefore, as the materials of the bottom part 43 and the wall part 44, the polymethylpentene is suitable.

Figure 5:
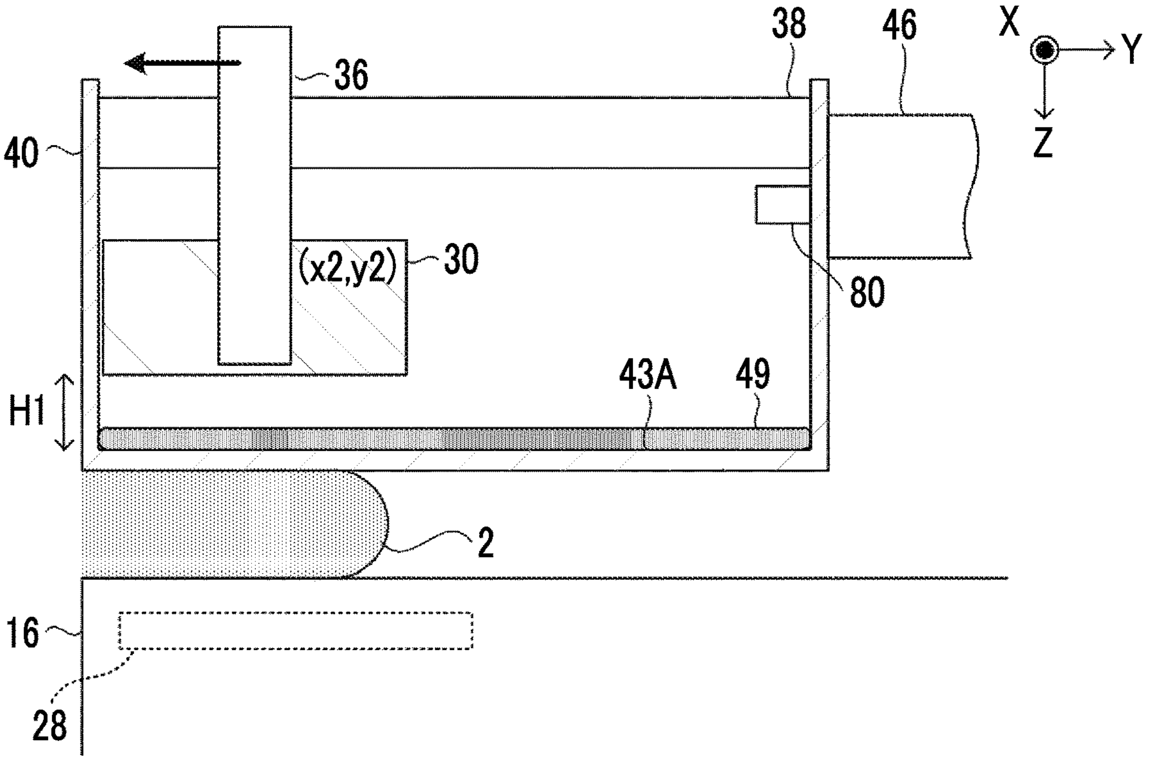
FIG. 5 is a view showing an example of the schematic configuration of the compression member.
Figure 6:
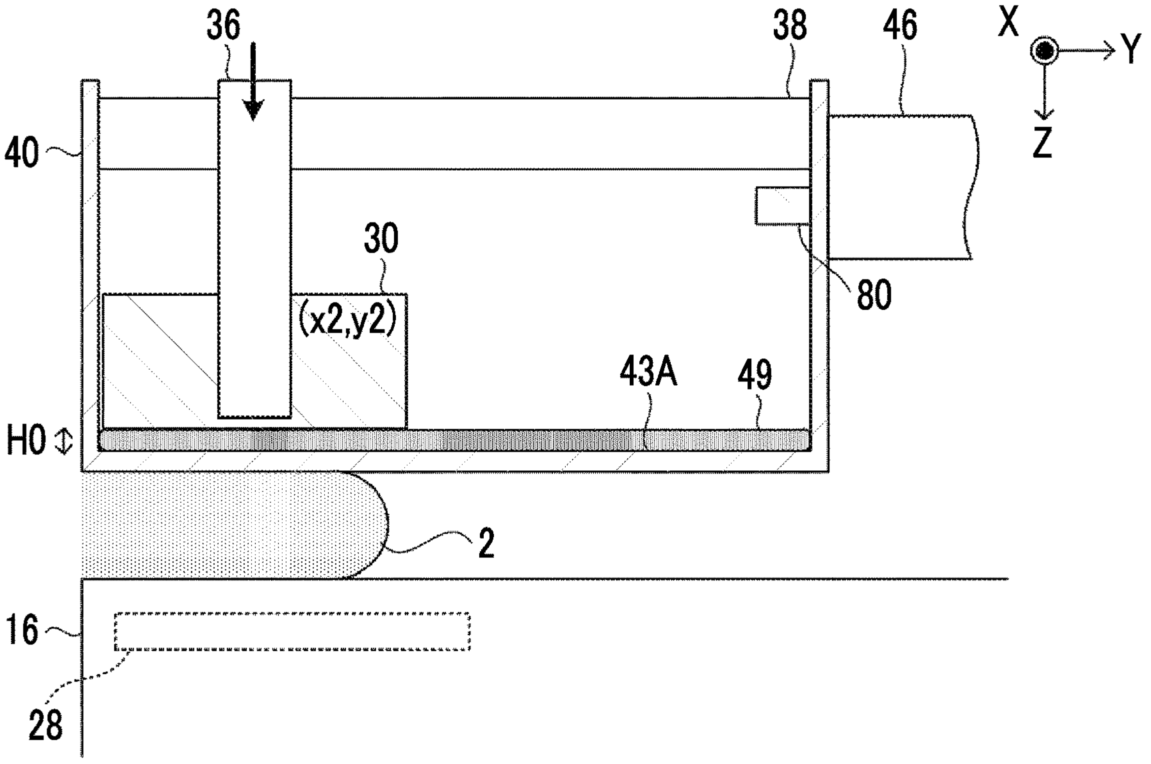
FIG. 6 is a view showing an example of the schematic configuration of the compression member.
Figure 7:
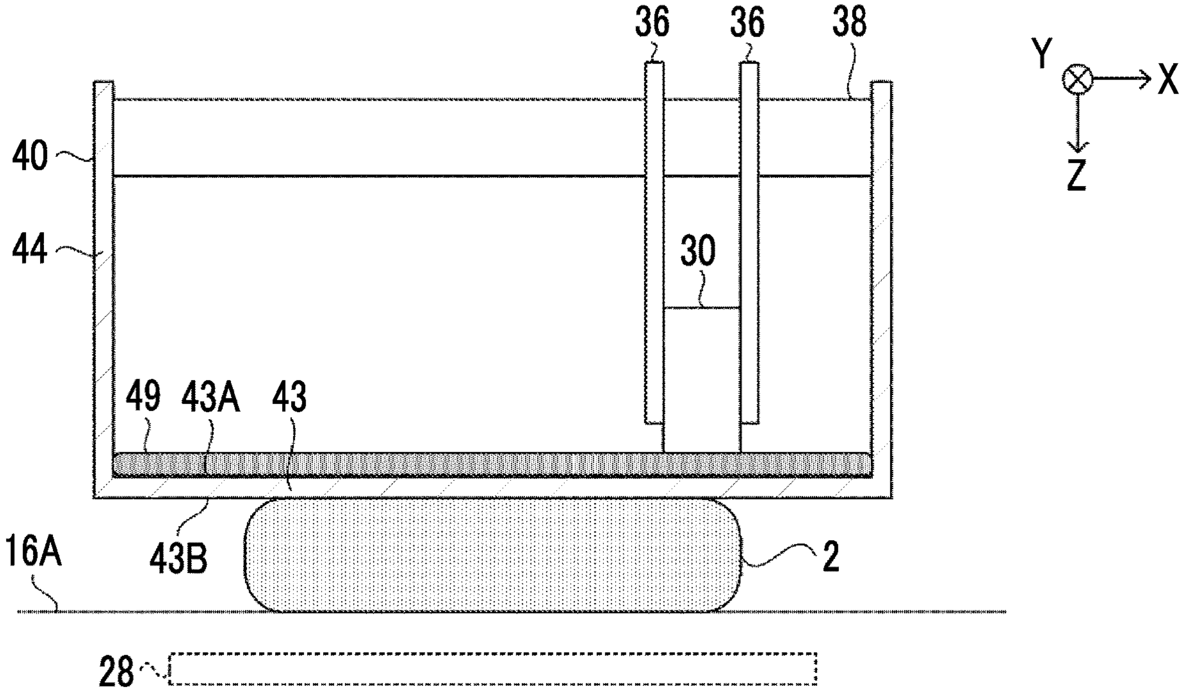
FIG. 7 is a view showing an example of the schematic configuration of the compression member.

The compression member 40 includes an ultrasound unit 30 inside a recess shape formed by the bottom part 43 and the wall part 44. FIGS. 3 to 7 show view showing a schematic configuration of an example of the compression member 40. FIGS. 3 to 6 are views of the compression member 40 as viewed from the right side of the examinee, and the positions of the ultrasound unit 30 inside the compression member 40 are different from each other. FIG. 7 is a view in a case in which the compression member 40 is viewed from a chest wall side toward a nipple side of the examinee.

As shown in FIGS. 3 to 7, the compression member 40 includes an ultrasound unit 30, a first drive mechanism 36, a second drive mechanism 38, and a distance measurement sensor 80 inside.

The ultrasound unit 30 captures the ultrasound image of a breast 2 put into the compressed state by the compression member 40 from an upper surface 43A side of the compression member 40 opposite to a contact surface 43B with the breast. In addition, the ultrasound unit 30 is configured to change a height H from the upper surface 43A by the first drive mechanism 36. The ultrasound unit 30 is configured to change an in-plane position (x, y) of the upper surface 43A in a plane direction by the second drive mechanism 38.

The first drive mechanism 36 moves the ultrasound unit 30 between at least two states of an approach state (see FIGS. 3 and 6) in which the ultrasound unit 30 approaches the upper surface 43A, and a separation state (see FIGS. 4 and 5) in which the ultrasound unit 30 is separated from the upper surface 43A as compared to the approach state. The ultrasound unit 30 according to the present embodiment captures the ultrasound image of the breast 2 in a case in which the ultrasound unit 30 is put into the approach state by the first drive mechanism 36, and does not capture the ultrasound image of the breast 2 in a case in which the ultrasound unit 30 is put into the separation state by the first drive mechanism 36.

Figure 3:
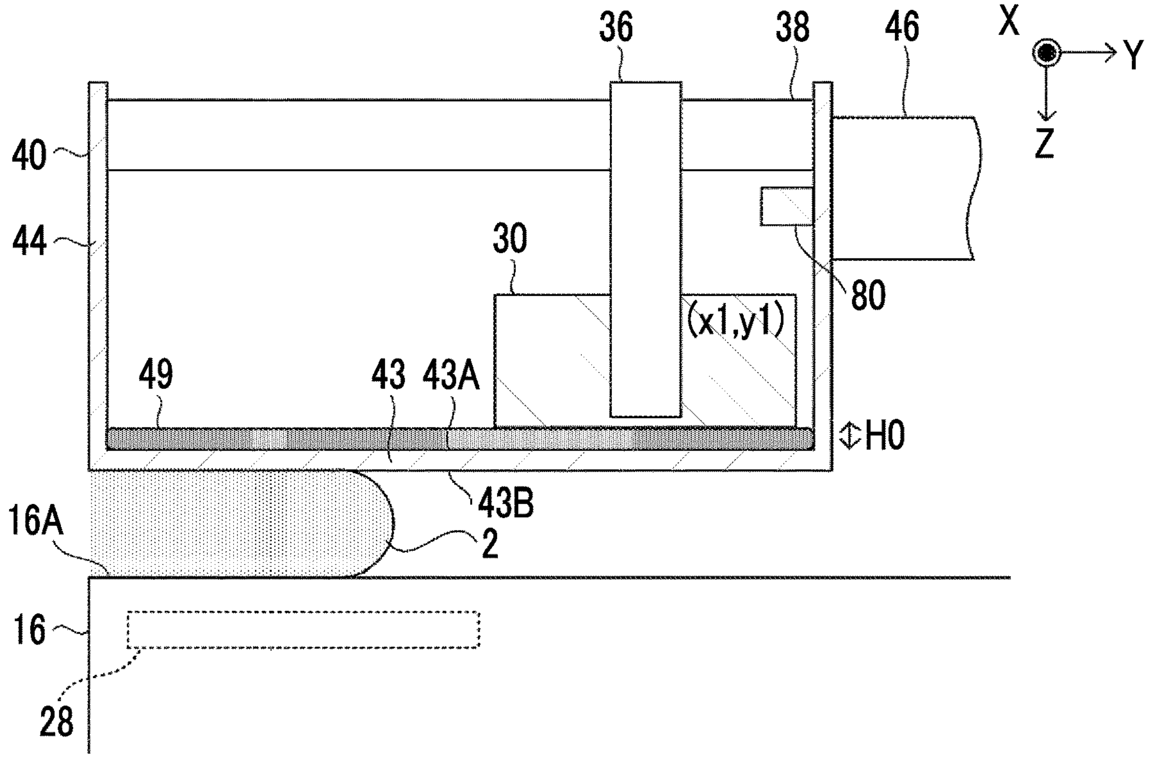
FIG. 3 is a view showing an example of a schematic configuration of a compression member.
Figure 4:
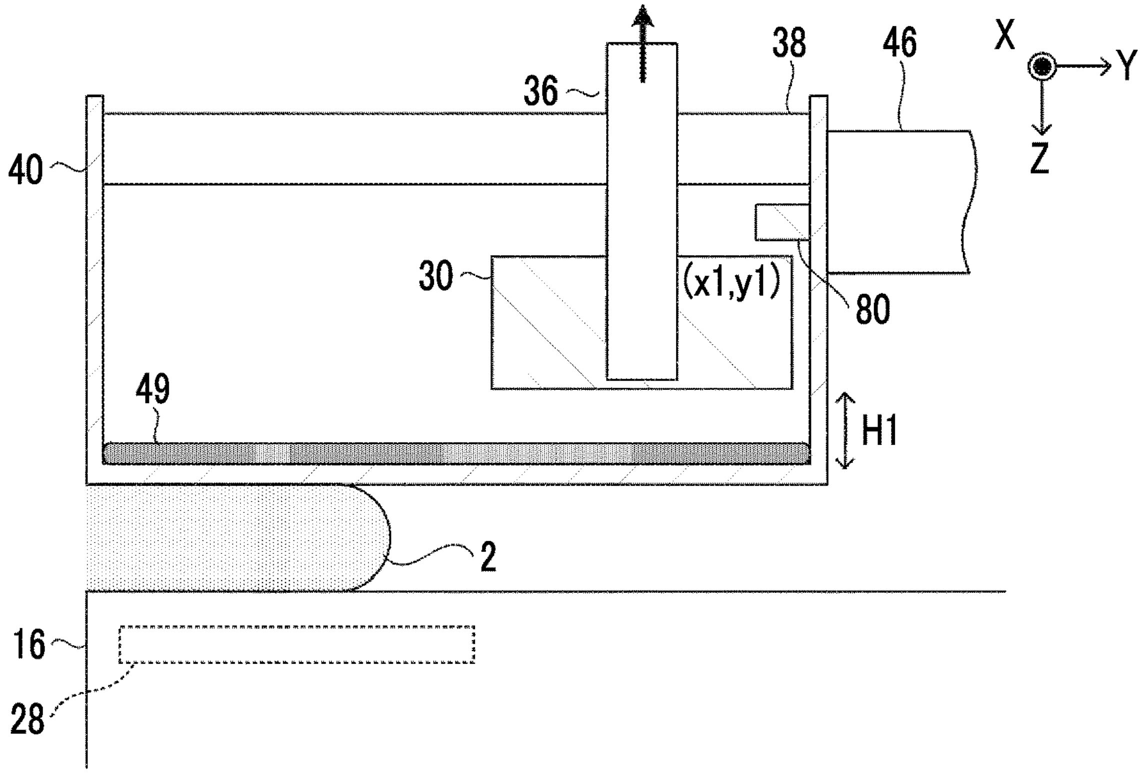
FIG. 4 is a view showing an example of the schematic configuration of the compression member.

For example, the first drive mechanism 36 vertically moves (raises) the ultrasound unit 30 from the approach state (height is H0) as shown in FIG. 3 to the separation state (height is H1) as shown in FIG. 4. In addition, for example, the first drive mechanism 36 vertically moves (lowers) the ultrasound unit 30 from the separation state (height is H1) as shown in FIG. 5 to the approach state (height is H0) as shown in FIG. 6. The first drive mechanism 36 is realized by, for example, a stepping motor as a drive source, and a belt or the like (none shown) that transmits the rotation of the motor to the ultrasound unit 30.

The second drive mechanism 38 moves the ultrasound unit 30 put into the separation state by the first drive mechanism 36, in the plane direction of the upper surface 43A. In the example of FIG. 3, the plane direction of the upper surface 43A is at least one of an X direction or a Y direction. For example, the second drive mechanism 38 moves the ultrasound unit 30 in a parallel manner from a position (x1, y1) close to the support part 46 in the separation state as in FIG. 4 to a position (x2, y2) away from the support part 46 in the separation state as in FIG. 5. The second drive mechanism 38 is realized by, for example, a stepping motor as a drive source, and a belt or the like (none shown) that transmits the rotation of the motor to the ultrasound unit 30.

The distance measurement sensor 80 includes a first sensor that detects the height H of the ultrasound unit 30 from the upper surface 43A, and a second sensor that detects the in-plane position (x, y) of the upper surface 43A of the ultrasound unit 30 in the plane direction. As such a sensor, for example, a laser imaging detection and ranging or light detection and ranging (LIDAR), a time-of-flight (TOF) camera, a stereo camera, or the like can be applied. The LIDAR and the TOF camera emit light, such as infrared light and visible light, and measure a distance based on a time until the reflected light is received or a phase change between the emitted light and the received light. The LIDAR measures a distance to an object to be measured by disposing a plurality of laser light emitters in a vertical direction and allowing each of the emitters to perform horizontally scanning (rotating). The TOF camera measures the distance to the object to be measured by emitting diffused light. The stereo camera measures the distance to the object to be measured by using a principle of triangulation based on a plurality of images obtained by imaging the object to be measured in different directions.

For example, a potentiometer or the like may be applied as the distance measurement sensor 80. The first sensor and the second sensor may be a combination of the same type or a combination of different types among various distance measurement sensors 80, such as the LIDAR, the TOF camera, the stereo camera, and the potentiometer. For example, in a case in which the LIDAR is used as the distance measurement sensor 80, both the height H and the in-plane position (x, y) of the ultrasound unit 30 can be detected by single unit.

Figure 8:
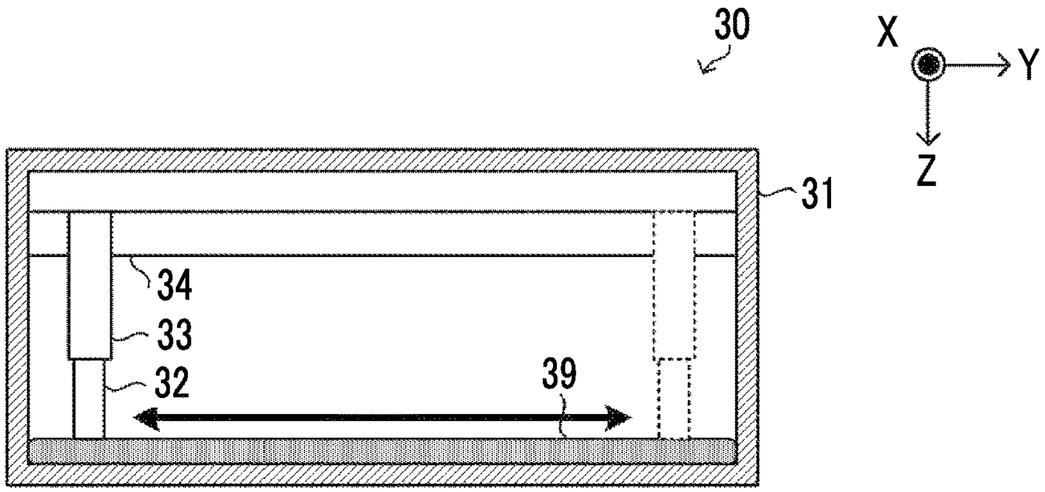
FIG. 8 is a view showing an example of a schematic configuration of an ultrasound unit.

Next, a description of the ultrasound unit 30 will be made in detail. FIG. 8 shows an example of a configuration of the ultrasound unit 30. As shown in FIG. 8, the ultrasound unit 30 comprises a case 31, an ultrasound probe 32, a support part 33, a scan mechanism 34, and a first medium 39.

The ultrasound probe 32 is accommodated in the case 31, and captures the ultrasound image of the breast 2 by irradiating the breast 2 with the ultrasound and receiving the reflected waves from the breast 2. Specifically, the ultrasound probe 32 comprises an ultrasound transducer array. The ultrasound transducer array is configured such that a plurality of ultrasound transducers are arranged one-dimensionally or two-dimensionally. The ultrasound transducer is formed, for example, such that electrodes are formed on both ends of a piezoelectric body, such as a piezoelectric ceramic represented by lead (Pb) zirconate titanate (PZT) or a polymer piezoelectric element represented by polyvinylidene difluoride (PVDF). The ultrasound unit 30 includes a converter (not shown) that converts the reflected waves from the breast received by the ultrasound probe 32 into the ultrasound image, and the ultrasound image is obtained by the converter.

The scan mechanism 34 is accommodated in the case 31 and moves the ultrasound probe 32 supported by the support part 33 in the case 31 in the plane direction of the upper surface 43A. The scan mechanism 34 is realized by, for example, a stepping motor as a drive source, and a belt or the like (none shown) that transmits the rotation of the motor to the ultrasound probe 32.

The first medium 39 is accommodated in the case 31 and is formed of a gel-like or liquid material having an ultrasound transmittance. Examples of such a material include a water-free gel substance, such as urethane rubber or silicone rubber, a polymer water-containing gel, such as polyvinyl alcohol or polyethylene oxide. By providing the first medium 39, it is possible to suppress entry of air into an interface between an ultrasound radiation surface of the ultrasound probe 32 and the case 31, and it is possible to reduce a difference in the acoustic impedance at the interface, so that the noise applied to the ultrasound image can be reduced. That is, the ultrasound probe 32 is moved in the plane direction of the upper surface 43A by the scan mechanism 34 in a state in which the ultrasound probe 32 is in contact with the case 31 via the first medium 39.

The ultrasound image may be captured by the ultrasound unit 30 in a state in which a gel-like or liquid second medium 49 having an ultrasound transmittance is applied on the upper surface 43A of the compression member 40. As such a medium, for example, a known jelly for an ultrasound examination, which has the acoustic impedance close to the acoustic impedance of the human body (breast), can be applied. That is, the ultrasound probe 32 included in the ultrasound unit 30 may capture the ultrasound image of the breast 2 via the first medium 39, the case 31, the second medium 49, and the bottom part 43 of the compression member 40.

By providing the second medium 49, it is possible to suppress entry of air into an interface between the case 31 of the ultrasound unit 30 and the upper surface 43A of the compression member 40, and it is possible to reduce a difference in the acoustic impedance at the interface, so that the noise applied to the ultrasound image can be reduced. As described above, the ultrasound unit 30 is moved in the plane direction by the second drive mechanism 38 after being put into the separation state by the first drive mechanism 36. That is, since the ultrasound unit 30 is not moved in the plane direction while being in contact with the second medium 49, there is no case in which the second medium 49 is biased and peeled off as the ultrasound unit 30 is moved in the plane direction. Accordingly, it is possible to maintain the above-described effect of the second medium 49, and it is possible to contribute to high-quality ultrasound imaging.

In addition, a movement speed of the ultrasound probe 32 in the plane direction caused by the scan mechanism 34 is lower than a movement speed of the ultrasound unit 30 in the plane direction caused by the second drive mechanism 38. For example, the movement speed of the ultrasound probe 32 in the plane direction caused by the scan mechanism 34 may be 10 mm per second, and the movement speed of the ultrasound unit 30 in the plane direction caused by the second drive mechanism 38 may be 100 mm per second. As described above, the movement speed of the ultrasound unit 30 in the plane direction caused by the second drive mechanism 38 is increased, whereby the time required for the ultrasound imaging can be reduced. Therefore, the compression time of the breast can also be reduced, and the pain of the examinee can be reduced. In addition, it is possible to perform highly accurate scanning by reducing the movement speed of the ultrasound probe 32 in the plane direction caused by the scan mechanism 34, and thus it is possible to contribute to high-quality ultrasound imaging.

It should be noted that the method of imaging the breast via the imaging apparatus 10 is not particularly limited. For example, cranio-caudal (CC) imaging, medio-lateral oblique (MLO) imaging, the magnification imaging and the spot imaging for imaging a part of the breast, and the like may be performed. The CC imaging is a method of imaging the breast in the compressed state by interposing the breast between the imaging table 16 and the compression member 40 in the up-down direction (Z direction). The MLO imaging is a method of imaging the breast in the compressed state including an axilla portion by interposing the breast between the imaging table 16 and the compression member 40 in a tilted state in which a rotation angle of the arm part 12 with respect to the base 14 is equal to or greater than 45 degrees and smaller than 90 degrees.

In addition, for example, the imaging apparatus 10 may perform tomosynthesis imaging. In the tomosynthesis imaging, the radiation R is emitted from each of a plurality of irradiation positions having different irradiation angles toward the breast by the radiation source 17R, to capture a plurality of radiation images of the breast. That is, in the tomosynthesis imaging, the imaging is performed by changing the rotation angle of the radiation emitting unit 17 with respect to the base 14 while fixing the angles of the imaging table 16, the compression member 40, the breast, and the like.

In addition, in the imaging apparatus 10, the breast of the examinee may be positioned not only in a state in which the examinee is standing (standing state) but also in a state in which the examinee is sitting on a chair, a wheelchair, or the like (sitting state).

Incidentally, in the practical operation of the imaging apparatus 10 that can capture the radiation image and the ultrasound image, it is conceivable to move the ultrasound unit 30 in order for the user, such as the doctor or the technician, to check the radiation image, to search for a region of interest, and to further check the region of interest in the ultrasound image. However, in a case in which the ultrasound unit 30 is manually moved, since the position of the region of interest cannot be specified from the appearance of the breast, it is difficult to quickly perform the ultrasound imaging including the region of interest.

Then, the console 50 according to the present embodiment has a function of supporting the ultrasound imaging in accordance with the region of interest specified from the radiation image. The console 50 controls the imaging apparatus 10 to capture the radiation image and the ultrasound image in accordance with the imaging order acquired from the RIS 6, the instruction from the user, and the like. Hereinafter, a description of the console 50 will be made.

Figure 9:
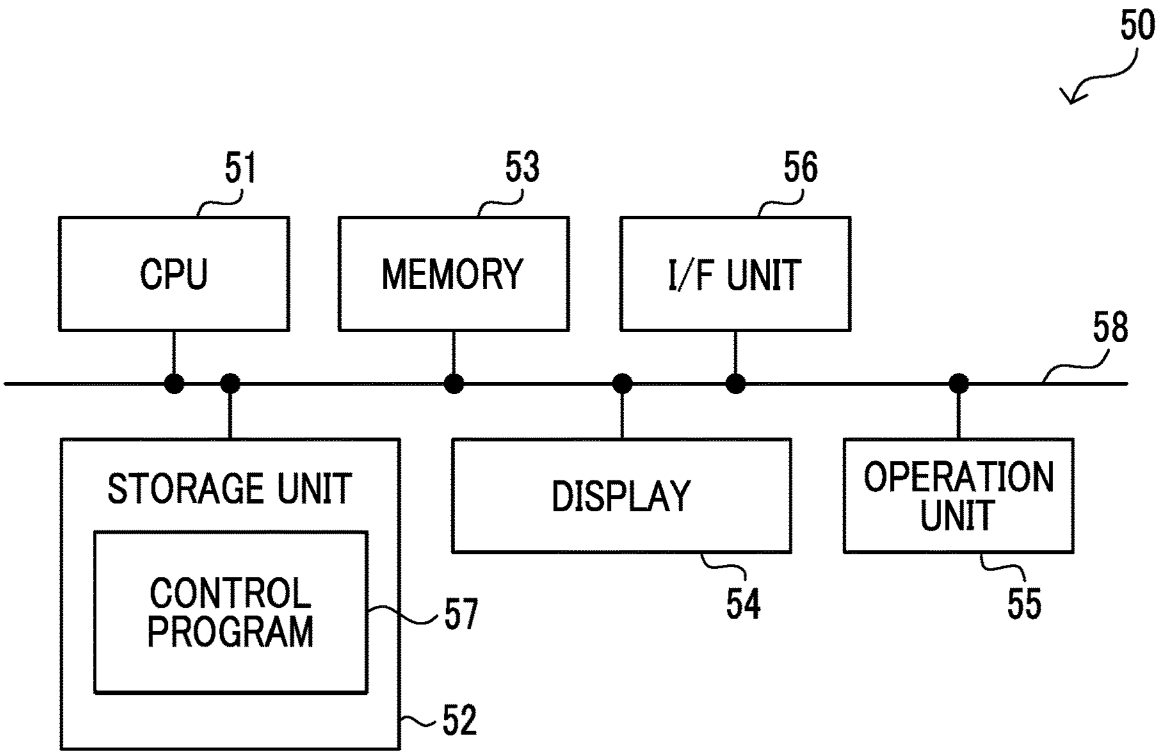
FIG. 9 is a block diagram showing an example of a hardware configuration of a console.

A description of an example of a hardware configuration of the console 50 will be made with reference to FIG. 9. As shown in FIG. 9, the console 50 includes a CPU 51, a non-volatile storage unit 52, and a memory 53 as a transitory storage region. In addition, the console 50 includes a display 54, such as a liquid crystal display, an operation unit 55, such as a touch panel, a keyboard, and a mouse, and an I/F unit 56. The I/F unit 56 performs wired or wireless communication with the imaging apparatus 10, the RIS 6, and other external apparatuses. The CPU 51, the storage unit 52, the memory 53, the display 54, the operation unit 55, and the I/F unit 56 are connected to each other via a bus 58, such as a system bus and a control bus, so that various types of information can be exchanged.

The storage unit 52 is realized by, for example, a storage medium, such as an HDD, an SSD, and a flash memory. A control program 57 in the console 50 is stored in the storage unit 52. The CPU 51 reads out the control program 57 from the storage unit 52 to deploy the control program 57 into the memory 53, and executes the deployed control program 57. As the console 50, for example, a personal computer, a server computer, a smartphone, a tablet terminal, a wearable terminal, or the like can be applied as appropriate.

In addition, the storage unit 52 stores the image data of the radiation image and the ultrasound image acquired by the imaging apparatus 10, various types of other information, and the like. The image data of the radiation image and the ultrasound image may be stored in association with at least one of the imaging order or the imaging information. The imaging information may be, for example, at least one of examinee information and an imaging item that are included in the imaging order, photographer information indicating a photographer (for example, the user, such as the doctor or the technician) who performs the imaging, or date and time information indicating date and time when the imaging is performed.

Figure 10:
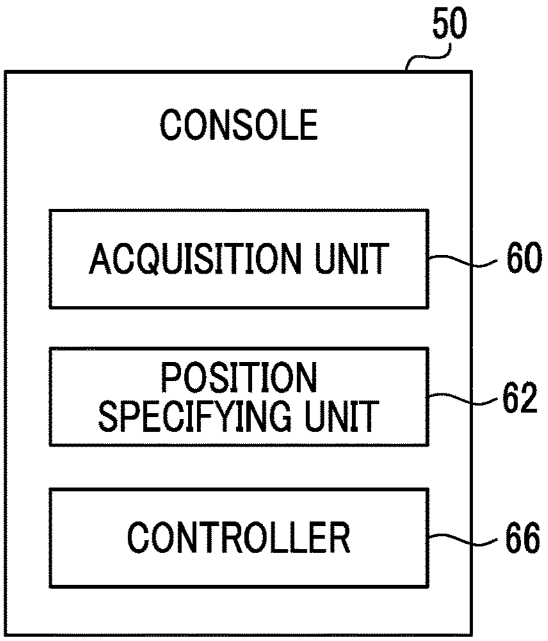
FIG. 10 is a block diagram showing an example of a functional configuration of the console according to a first embodiment.

A description of an example of a functional configuration of the console 50 will be made with reference to FIG. 10. As shown in FIG. 10, the console 50 includes an acquisition unit 60, a position specifying unit 62, and a controller 66. In a case in which the CPU 51 executes the control program 57, the CPU 51 functions as the acquisition unit 60, the position specifying unit 62, and the controller 66.

Figure 11:
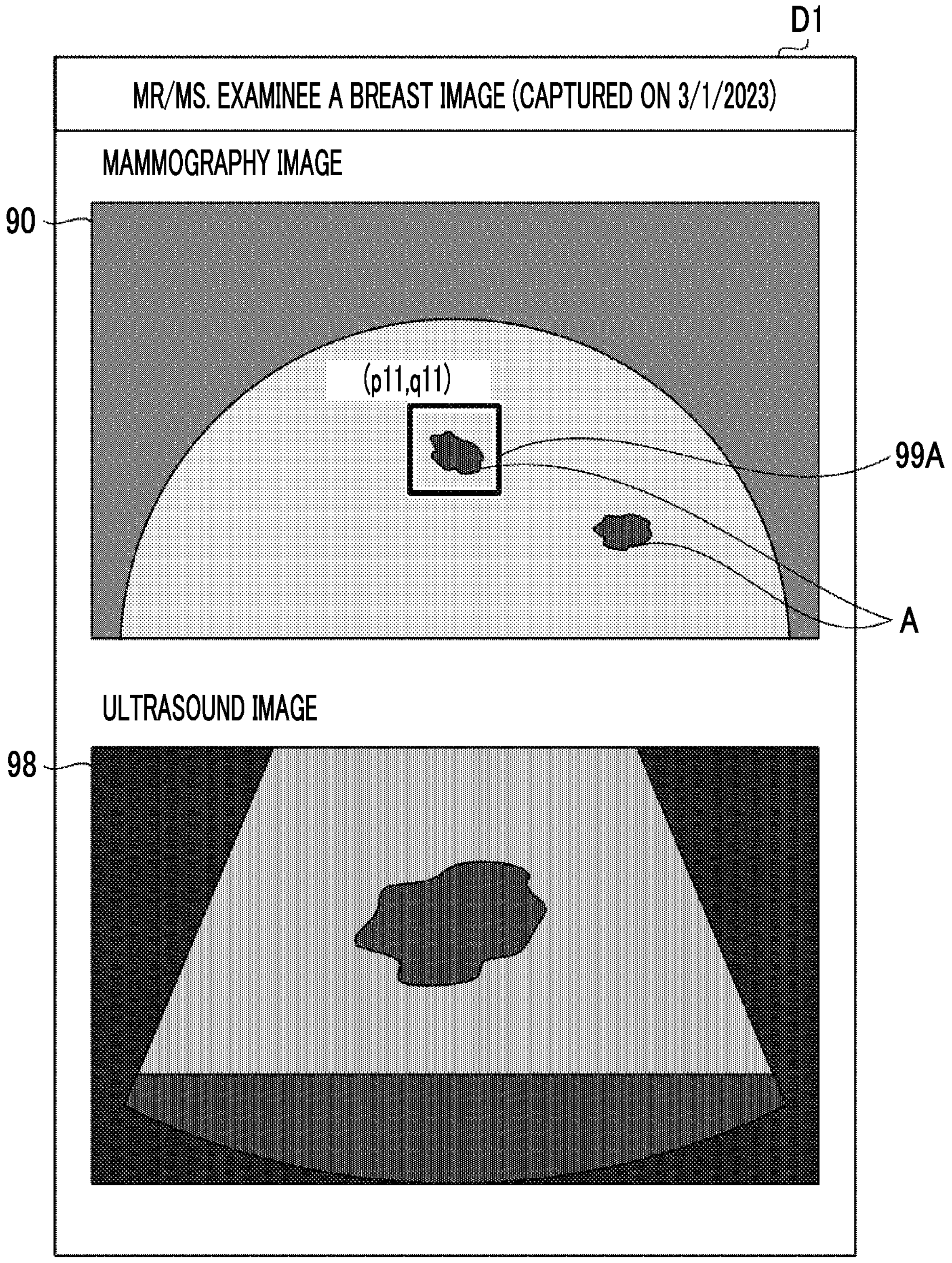
FIG. 11 is a view showing an example of a screen displayed on a display.
Figure 12:
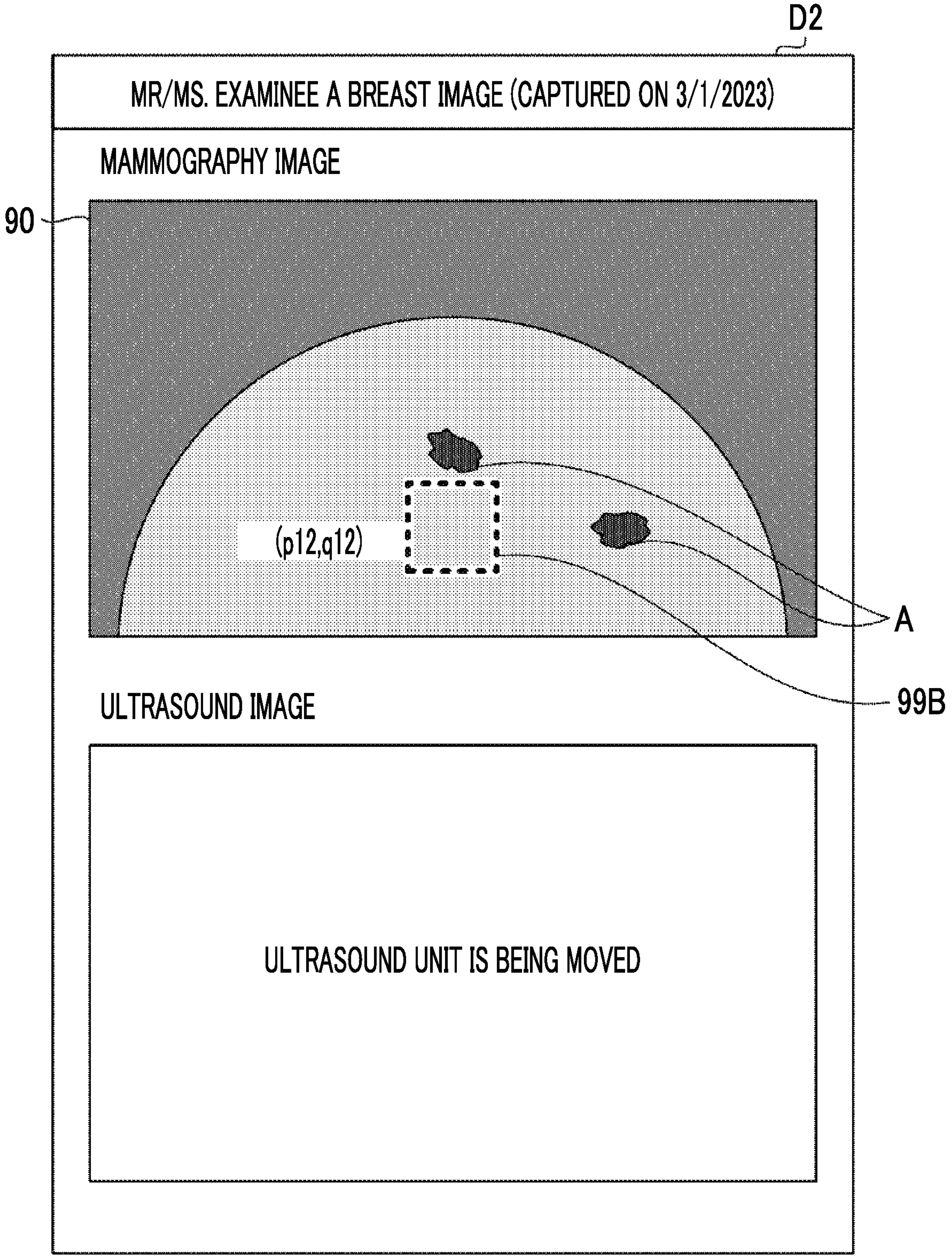
FIG. 12 is a view showing an example of the screen displayed on the display.
Figure 13:
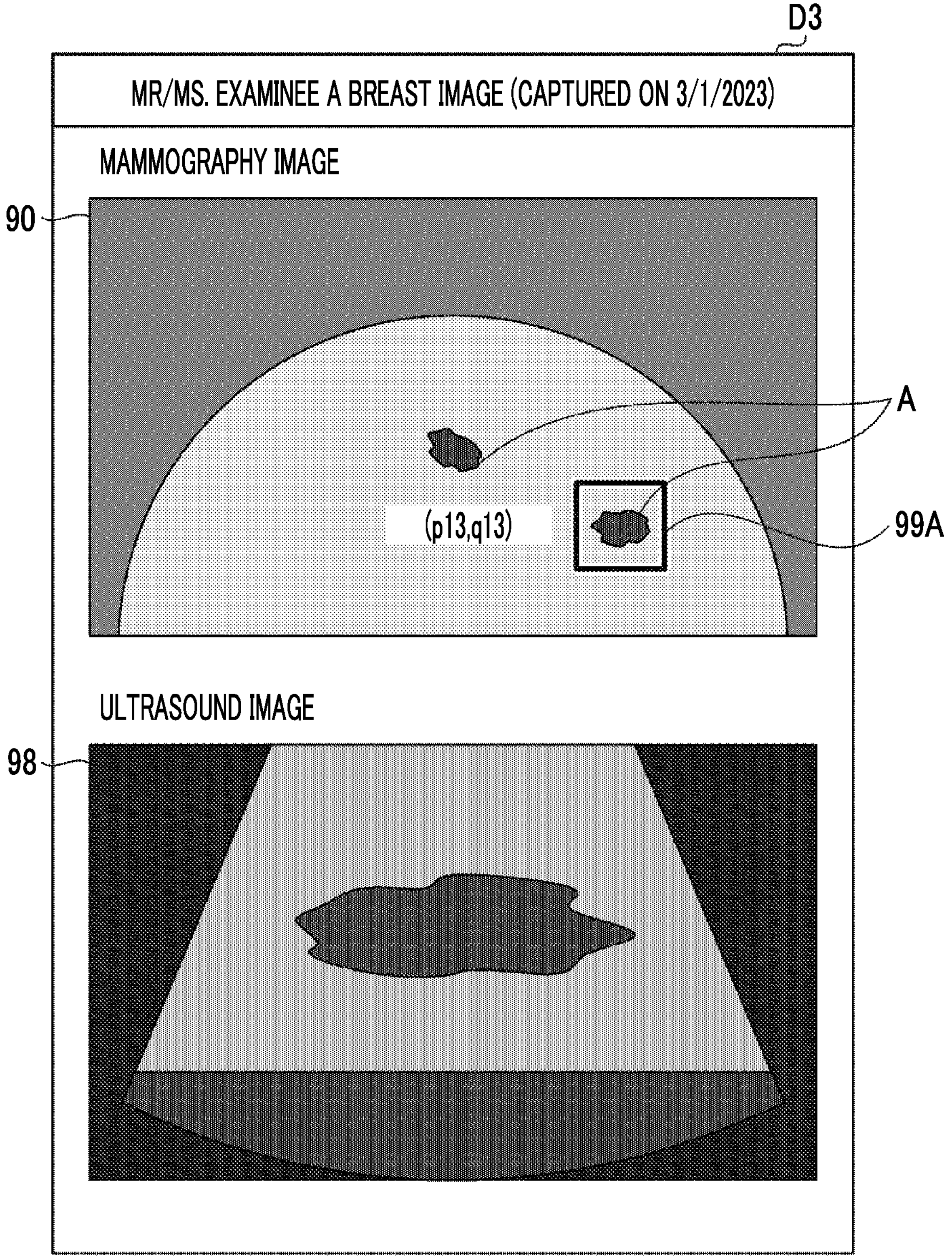
FIG. 13 is a view showing an example of the screen displayed on the display.

A description of a method of supporting the ultrasound imaging will be made with reference to FIGS. 11 to 13. FIGS. 11 to 13 are examples of screens D1 to D3 displayed on the display 54 by the controller 66. On the screens D1 to D3, a radiation image 90 (mammography image) is displayed in an upper part, and an ultrasound image 98 is displayed in a lower part. In addition, a current position of the ultrasound unit 30 is displayed in a state of being superimposed on the radiation image 90 by a first marker 99A or a second marker 99B.

FIG. 11 shows a state in which the ultrasound unit 30 is in the approach state, but a range of the ultrasound imaging does not coincide with a region of interest A. FIG. 12 shows a state in which the ultrasound unit 30 is in the separation state and the ultrasound unit 30 is being moved in the plane direction. FIG. 13 shows a state in which the ultrasound unit 30 is in the approach state and the range of the ultrasound imaging coincides with the region of interest A.

The acquisition unit 60 acquires the radiation image 90 of the breast 2 put into the compressed state by the compression member 40 from the imaging apparatus 10. Specifically, the acquisition unit 60 may acquire the radiation image 90 stored in the storage unit 22 of the imaging apparatus 10 via the I/F unit 56, may acquire the radiation image 90 stored in the storage unit 52, or may acquire the radiation image 90 stored in the external apparatus.

The acquisition unit 60 associates coordinates (p, q) of the acquired radiation image 90 with the in-plane position (x, y) of the ultrasound unit 30 in the plane direction of the upper surface 43A of the compression member 40. That is, the acquisition unit 60 specifies to which coordinates (p, q) of the radiation image the actual position (x, y) of the ultrasound unit 30 in the plane direction corresponds, for all positions in a movable range of the ultrasound unit 30. This association can be obtained, for example, in accordance with to the size and the position of the irradiation field in a case in which the radiation image is captured. The result of associating the coordinates (p, q) of the radiation image with the in-plane position (x, y) is stored in, for example, the storage unit 52 or the like.

In addition, the acquisition unit 60 acquires, in an order of time, height information indicating the height H of the ultrasound unit 30 from the upper surface 43A of the compression member 40 detected by the distance measurement sensor 80 (first sensor). In addition, the acquisition unit 60 acquires, in an order of time, the in-plane position (x, y) of the ultrasound unit 30 in the plane direction of the upper surface 43A of the compression member 40 detected by the distance measurement sensor 80 (second sensor).

The position specifying unit 62 determines whether or not the ultrasound unit 30 is put into the approach state based on the height H indicated by the height information acquired by the acquisition unit 60. Specifically, the position specifying unit 62 determines whether or not the height H indicated by the height information acquired by the acquisition unit 60 satisfies a predetermined condition.

For example, as the condition, the position specifying unit 62 may determine whether or not a temporal change amount of the height H of the ultrasound unit 30 from the upper surface 43A in a predetermined period is equal to or greater than a predetermined threshold value. In a case in which the height H of the ultrasound unit 30 from the upper surface 43A is changed by an amount equal to or greater than the predetermined threshold value (for example, 3 cm) in the predetermined period (for example, 1 second), it is considered that the ultrasound unit 30 is intentionally lowered for the ultrasound imaging. With such a condition, for example, minute shake or the like of the height H accompanying the movement or the like of the ultrasound unit 30 in the plane direction can be excluded.

In addition, for example, the position specifying unit 62 may determine whether or not the absolute value of the height H of the ultrasound unit 30 from the upper surface 43A is smaller than the predetermined threshold value (for example, 5 mm), as the condition. As the threshold value in this case, the maximum value that can be regarded as the approach state can be set.

Case in which Approach State is Determined

A description of a case in which the ultrasound unit 30 is in the approach state will be made with reference to FIG. 11. In a case in which the position specifying unit 62 determines that the height H indicated by the height information satisfies the condition, the position specifying unit 62 specifies a first position, which is the in-plane position (x, y) of the ultrasound unit 30, in the predetermined period including a point in time at which the condition is satisfied. For example, in a case in which the in-plane position of the ultrasound unit 30 is (x11, y11) at a point in time at which the ultrasound unit 30 is put into the approach state for the ultrasound imaging (or may be a period before and after the point in time), the position specifying unit 62 sets the position at (x11, y11) as the first position. In addition, the position specifying unit 62 refers to the result of associating the coordinates (p, q) of the radiation image with the in-plane position (x, y), and specifies first coordinates (p11, q11) of the radiation image corresponding to the specified first position (x11, y11).

The controller 66 performs control of displaying, on the display 54, the first marker 99A indicating the first coordinates (p11, q11) specified by the position specifying unit 62 in a state of being superimposed on the radiation image 90 acquired by the acquisition unit 60.

Case in which Separation State is Determined

A description of a case in which the ultrasound unit 30 is in the separation state will be made with reference to FIG. 12. In a case in which the position specifying unit 62 determines that the height H indicated by the height information does not satisfy the condition, the position specifying unit 62 specifies a second position, which is the in-plane position (x, y) of the ultrasound unit 30, in the predetermined period including a point in time at which the condition is not satisfied. For example, in a case in which the in-plane position of the ultrasound unit 30 is (x12, y12) at a point in time at which the ultrasound unit 30 is put into the separation state for moving the ultrasound unit 30 (or may be a period before and after the point in time), the position specifying unit 62 sets the position at (x12, y12) as the second position. In addition, the position specifying unit 62 refers to the result of associating the coordinates (p, q) of the radiation image with the in-plane position (x, y), and specifies second coordinates (p12, q12) of the radiation image corresponding to the specified second position (x12, y12).

The controller 66 performs control of displaying, on the display 54, the second marker 99B, which has a different form from the first marker 99A and indicates the second coordinates (p12, q12) specified by the position specifying unit 62, in a state of being superimposed on the radiation image 90 acquired by the acquisition unit 60. As an example, FIGS. 11 and 12 show examples in which the first marker 99A is a solid line and the second marker 99B is a broken line. It should be noted that, as long as it can be seen that the first marker 99A and the second marker 99B indicate different values, for example, the colors, line types, thicknesses, shapes, and the like of the markers may be different from each other. The forms of the first marker 99A and the second marker 99B are made different, so that it is easy to understand whether the current state is the approach state or the separation state. In addition, as described above, in the separation state, the ultrasound imaging is not performed, and thus the ultrasound image 98 is not displayed on the screen D2.

Case in which Approach State is Determined Again

A description of a case in which it is determined that the ultrasound unit 30 is in the approach state again will be made with reference to FIG. 13. In a case in which the ultrasound unit 30 is put into the approach state again after being temporarily put into the separation state, it is considered that the ultrasound imaging is performed on another region of interest A. Even in this case, in a case in which the position specifying unit 62 determines that the height H indicated by the height information satisfies the condition, the position specifying unit 62 specifies the first position, which is the in-plane position (x, y) of the ultrasound unit 30, in the predetermined period including the point in time at which the condition is satisfied. For example, in a case in which the in-plane position of the ultrasound unit 30 is (x13, y13) at a point in time at which the ultrasound unit 30 is put into the approach state for the ultrasound imaging (or may be the period before and after the point in time), the position specifying unit 62 sets the position at (x13, y13) as the first position. In addition, the position specifying unit 62 refers to the result of associating the coordinates (p, q) of the radiation image with the in-plane position (x, y), and specifics first coordinates (p13, q13) of the radiation image corresponding to the specified first position (x13, y13).

The controller 66 performs control of displaying, on the display 54, the first marker 99A indicating the first coordinates (p13, q13) specified by the position specifying unit 62 in a state of being superimposed on the radiation image 90 acquired by the acquisition unit 60. In this way, each time the approach state is determined, the position specifying unit 62 specifies the first position of the ultrasound unit 30 and the first coordinates of the radiation image corresponding to the first position.

In addition, the controller 66 may perform control of storing the radiation image 90 and the first coordinates specified by the position specifying unit 62 in the storage unit 52 in association with each other.

Figure 14:
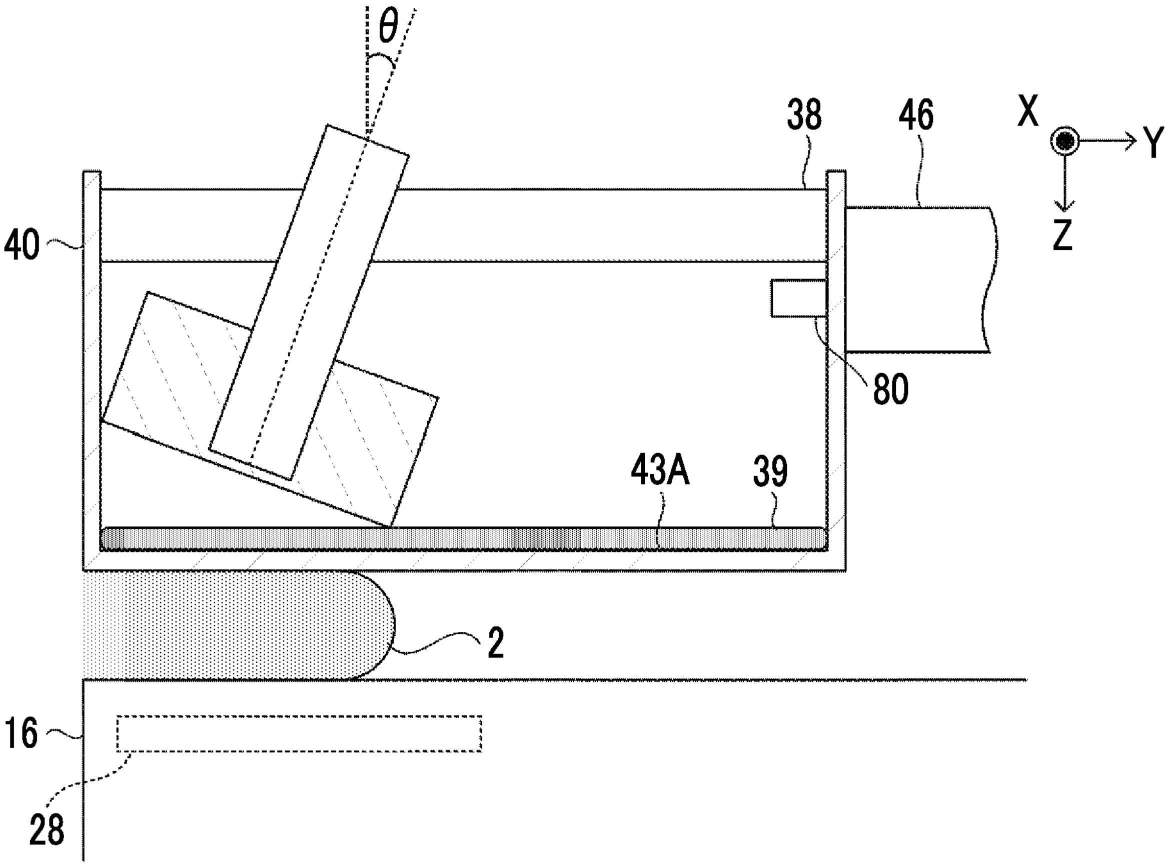
FIG. 14 is a view showing an example of the schematic configuration of the compression member.
Figure 15:
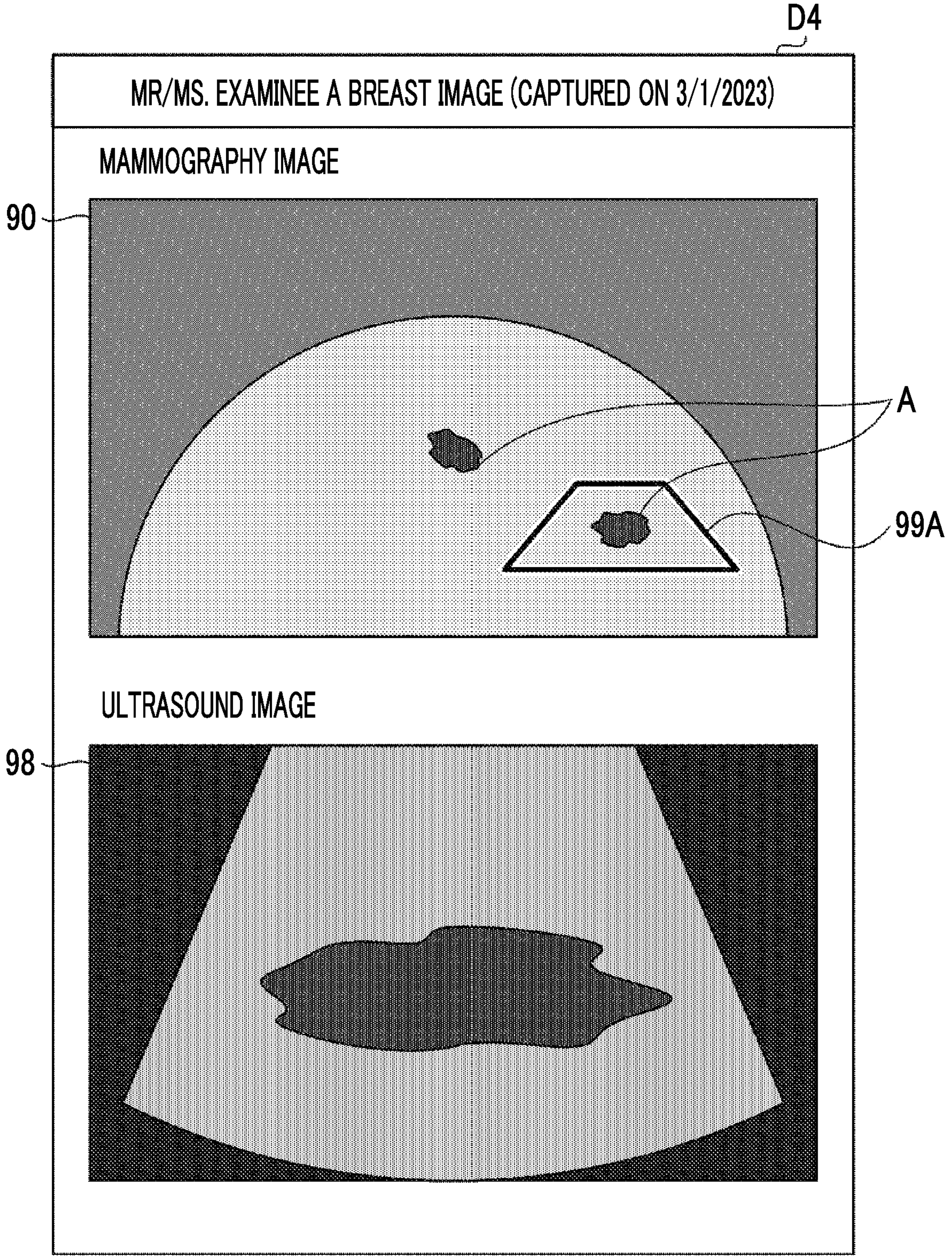
FIG. 15 is a view showing an example of the screen displayed on the display.

It should be noted that, in the ultrasound imaging, as shown in FIG. 14, the imaging may be performed in a state in which the ultrasound unit 30 is inclined with respect to the upper surface 43A. In this case, as shown in FIG. 15, a range of the obtained ultrasound image is different from a range in a case in which the ultrasound unit 30 is vertically applied to the upper surface 43A (see FIG. 13).

Then, in a case in which the position specifying unit 62 determines that the height H indicated by the height information satisfies the condition (that is, in the approach state), it is desirable that the position specifying unit 62 specifies an angle θ of the ultrasound unit 30 with respect to the upper surface 43A in the predetermined period including the point in time at which the condition is satisfied, in addition to the first position. In addition, as shown in FIG. 15, the position specifying unit 62 may specify the first coordinates of the radiation image corresponding to the first position in consideration of the angle θ.

Figure 16:
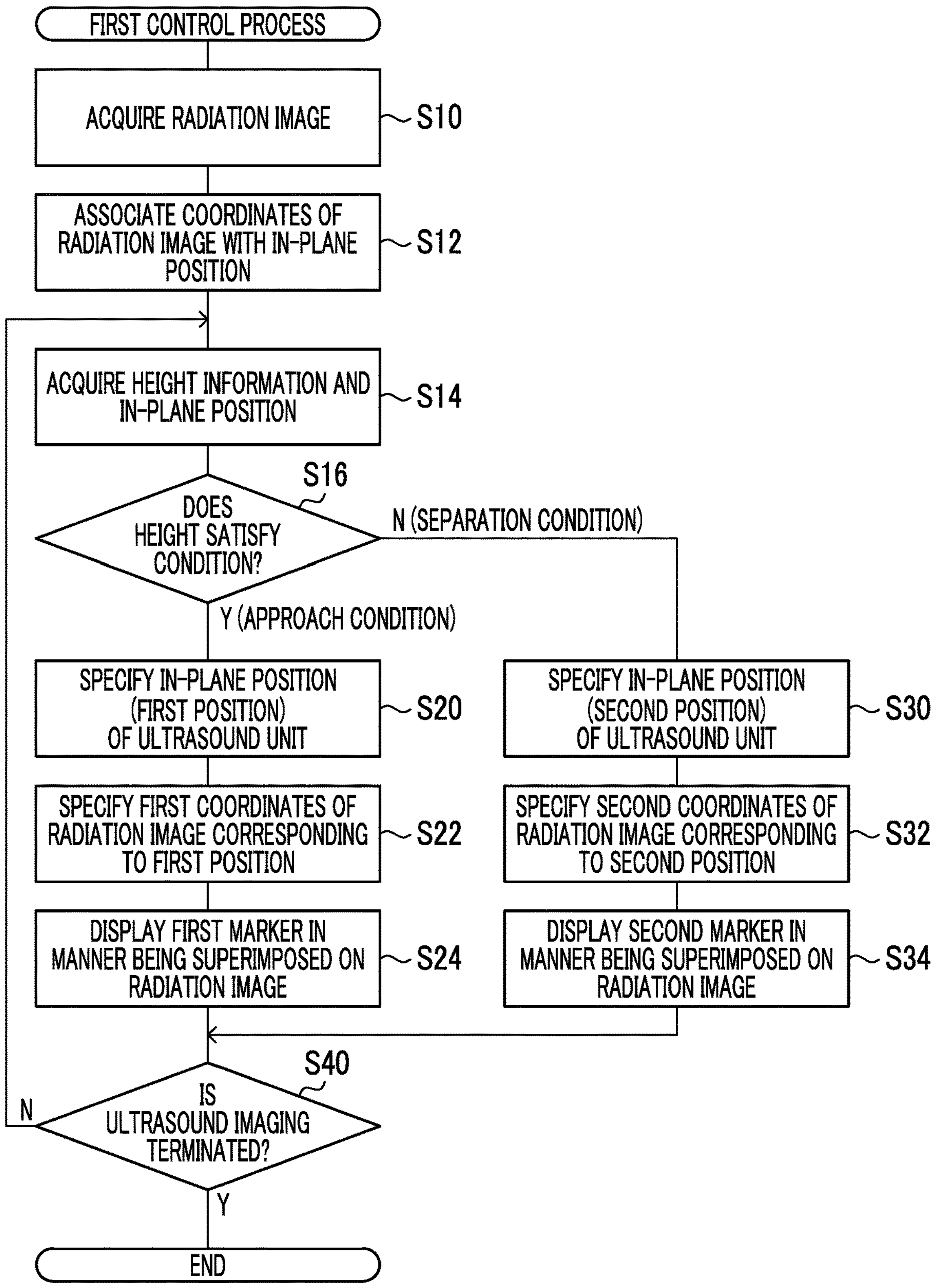
FIG. 16 is a flowchart showing an example of a first control process.

Next, a description of an action of the console 50 according to the present embodiment will be made with reference to FIG. 16. In the console 50, the CPU 51 executes the control program 57 to execute a first control process shown in FIG. 16. The first control process is executed, for example, in a case in which the user gives an instruction to start the execution via the operation unit 55.

In step S10, the acquisition unit 60 acquires the radiation image captured by the imaging apparatus 10. In step S12, the acquisition unit 60 associates the coordinates (p, q) of the radiation image acquired in step S10 with the in-plane position (x, y) of the ultrasound unit 30 in the plane direction of the upper surface 43A of the compression member 40.

In step S14, the acquisition unit 60 acquires the height information indicating the height H of the ultrasound unit 30 from the upper surface 43A of the compression member 40 detected by the distance measurement sensor 80 (first sensor). In addition, the acquisition unit 60 acquires, in an order of time, the in-plane position (x, y) of the ultrasound unit 30 in the plane direction of the upper surface 43A of the compression member 40 detected by the distance measurement sensor 80 (second sensor). In step S16, the position specifying unit 62 determines whether or not the height H indicated by the height information acquired in step S14 satisfies the predetermined condition.

In a case in which an affirmative determination is made in step S16, the approach state is determined, the process proceeds to step S20, and the position specifying unit 62 specifies, as the first position, the in-plane position (x, y) of the ultrasound unit 30, in the predetermined period including a point in time at which the condition is satisfied. In step S22, the position specifying unit 62 specifies the first coordinates (p, q) of the radiation image corresponding to the first position (x, y) specified in step S20 with reference to the result of association in step S12. In step S24, the controller 66 displays, on the display 54, the first marker 99A corresponding to the first coordinates (p, q) specified in step S22 in a state of being superimposed on the radiation image acquired in step S10.

On the other hand, in a case in which a negative determination is made in step S16, the separation state is determined, the process proceeds to step S30, and the position specifying unit 62 specifies, as the second position, the in-plane position (x, y) of the ultrasound unit 30, in the predetermined period including a point in time at which it is determined that the condition is not satisfied. In step S32, the position specifying unit 62 specifies the second coordinates (p, q) of the radiation image corresponding to the second position (x, y) specified in step S30 with reference to the result of association in step S12. In step S34, the controller 66 displays, on the display 54, the second marker 99B corresponding to the second coordinates (p, q) specified in step S32 in a state of being superimposed on the radiation image acquired in step S10.

In a case in which step S24 or S34 is completed, the process proceeds to step S40. In step S40, the controller 66 determines whether or not the ultrasound imaging is terminated for the breast that is the examination target. In this determination, for example, a determination may be made by allowing the user to input whether or not to terminate the ultrasound imaging, or may be made in accordance with whether there is another region of interest in the radiation image acquired in step S10. In a case in which an affirmative determination is made in step S40, the first control process is terminated as it is. In a case in which a negative determination is made in step S40, the process returns to step S14.

As described above, the imaging apparatus 10 according to the aspect of the present disclosure comprises the imaging table 16 having the imaging surface 16A, the compression member 40 for putting the breast 2 disposed on the imaging surface 16A into the compressed state, the ultrasound unit 30 that captures the ultrasound image 98 of the breast 2 put into the compressed state by the compression member 40, from the upper surface 43A side of the compression member 40 opposite to the contact surface 43B with the breast 2, the first drive mechanism 36 that moves the ultrasound unit 30 between at least two states of the approach state in which the ultrasound unit 30 approaches the upper surface 43A, and the separation state in which the ultrasound unit 30 is separated from the upper surface 43A as compared to the approach state, and the second drive mechanism 38 that moves the ultrasound unit 30 put into the separation state by the first drive mechanism 36, in the plane direction of the upper surface 43A.

With the imaging apparatus 10, the movement of the ultrasound unit 30 in the plane direction of the upper surface 43A is performed in the separation state, whereby the time required for the ultrasound imaging can be reduced. Therefore, the compression time of the breast can be reduced, and the pain of the examinee can be reduced. In addition, even in a case in which the second medium 49 is provided in order to suppress entry of air into the interface between the case 31 of the ultrasound unit 30 and the upper surface 43A of the compression member 40, since the ultrasound unit 30 is not moved in the plane direction while being in contact with the second medium 49, there is no case in which the second medium 49 is peeled off. Therefore, it is possible to maintain the effect of reducing the noise applied to the ultrasound image obtained by the second medium 49, and it is possible to contribute to high-quality ultrasound imaging. As described above, with the imaging apparatus 10 according to the aspect of the present disclosure, it is possible to support the ultrasound imaging.

In addition, the console 50 according to the aspect of the present disclosure comprises at least one processor, and the processor acquires, in an order of time, for the ultrasound unit 30 that captures the ultrasound image 98 of the breast 2 put into the compressed state by the compression member 40, is disposed on the upper surface 43A side of the compression member 40 opposite to the contact surface 43B with the breast 2, and has the in-plane position in the plane direction of the upper surface 43A and the height from the upper surface 43A, which are changeable, the height information indicating the height from the upper surface 43A, determines whether or not the height is indicated by the height information satisfies the predetermined condition, and in a case in which it is determined that the height H indicated by the height information satisfies the condition, specifies the first position, which is the in-plane position of the ultrasound unit 30, in the predetermined period including the point in time at which the condition is satisfied.

That is, the console 50 determines whether or not the ultrasound imaging is performed (whether in the approach state or the separation state) based on the height of the ultrasound unit 30 from the upper surface 43A, and specifies the position of the ultrasound unit 30 in the plane direction triggered by the determination that the ultrasound imaging is performed. Accordingly, since it is possible to acquire the in-plane position in a case in which the ultrasound unit 30 is located at the height of the predetermined condition, the comparative image interpretation can be performed while performing the registration between the radiation image and the ultrasound image, so that it is possible to support the ultrasound imaging.

It should be noted that the functions of the acquisition unit 60, the position specifying unit 62, and the controller 66 of the console 50 according to the present embodiment can be applied to an imaging apparatus having a configuration other than the imaging apparatus 10 described in the embodiment. For example, the functions can be applied even to the imaging apparatus that does not comprise the first drive mechanism 36 and the second drive mechanism 38, and moves the ultrasound unit 30 in the height direction (Z direction) and the plane direction (X direction and Y direction) freehand.

Second Embodiment

In the first embodiment, the form is described in which the time required for search for the region of interest is reduced by displaying the first marker 99A and the second marker 99B corresponding to the position of the ultrasound unit 30 in the plane direction in a state of being superimposed on the radiation image 90. This method can also be applied to a case in which the ultrasound unit 30 is manually moved. However, in order to further speed up the ultrasound imaging, it is desirable to perform control of automatically moving the ultrasound unit 30 in accordance with the position of the region of interest included in the radiation image 90.

Figure 17:
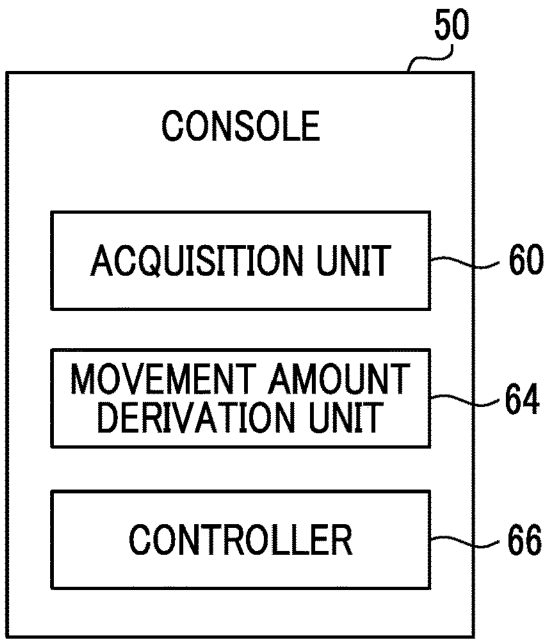
FIG. 17 is a block diagram showing an example of a functional configuration of a console according to a second embodiment.

Hereinafter, a description of the function of the console 50 according to the present embodiment having the function of the automatic registration will be made. In addition, the description of the same functions and configurations as the functions and configurations of the first embodiment will be omitted. As shown in FIG. 17, the console 50 according to the present embodiment includes the acquisition unit 60, a movement amount derivation unit 64, and the controller 66. In a case in which the CPU 51 executes the control program 57, the CPU 51 functions as the acquisition unit 60, the movement amount derivation unit 64, and the controller 66.

The acquisition unit 60 acquires the radiation image 90 of the breast 2 put into the compressed state by the compression member 40 from the imaging apparatus 10.

The movement amount derivation unit 64 specifies the position of the region of interest A in the radiation image 90 acquired by the acquisition unit 60. The position of the region of interest A is indicated by coordinates (pa, qa) of the radiation image 90.

For example, the movement amount derivation unit 64 may extract the region of interest A in the radiation image 90 by applying a method using a known computer aided detection/diagnosis (CAD) technique as appropriate. As the method of extracting the region of interest using the CAD technique, for example, a method using a learning model, such as a convolutional neural network (CNN), may be applied. For example, the movement amount derivation unit 64 may specify the position of the region of interest in the radiation image 90 by using a learning model trained to receive the radiation image 90 as an input and then extract and output the region of interest included in the radiation image 90.

In addition, for example, the movement amount derivation unit 64 may perform control of displaying the radiation image 90 on the display 54, and may receive the designation of the position of the region of interest A in the radiation image 90 by the user. The user may check the radiation image 90 and designate the position of the region of interest included in the radiation image 90 via the operation unit 55.

The movement amount derivation unit 64 derives the movement amount of the ultrasound unit 30 caused by the second drive mechanism 38 in accordance with the specified position (pa, qa) of the region of interest A in the radiation image 90. Specifically, the movement amount derivation unit 64 refers to the result (see the first embodiment) of associating the coordinates (p, q) of the radiation image with the in-plane position (x, y), and specifies the in-plane position (xa, ya) corresponding to the specified position (pa, qa) of the region of interest A. Then, the movement amount derivation unit 64 derives the movement amount from a current in-plane position of the ultrasound unit 30 to the specified in-plane position (xa, ya).

The controller 66 performs control of driving the second drive mechanism 38 in accordance with the movement amount derived by the movement amount derivation unit 64.

It should be noted that it is desirable that the controller 66 performs the control of driving the second drive mechanism 38 so that the ultrasound unit 30 is moved outside the irradiation field of the radiation R in the predetermined period including the period in which the breast 2 is irradiated with the radiation R by the radiation source 17R with the radiation R. This is for preventing the ultrasound unit 30 from being imaged in the radiation image 90.

Figure 18:
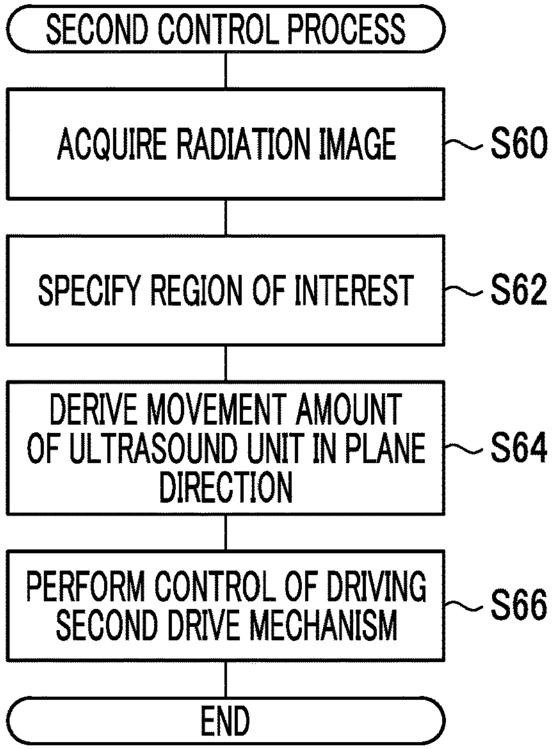
FIG. 18 is a flowchart showing an example of a second control process.

Next, a description of an action of the console 50 according to the present embodiment will be made with reference to FIG. 18. In the console 50, the CPU 51 executes the control program 57 to execute a second control process shown in FIG. 18. The second control process is executed, for example, in a case in which the user gives an instruction to start the execution via the operation unit 55.

In step S60, the acquisition unit 60 acquires the radiation image captured by the imaging apparatus 10. In step S62, the movement amount derivation unit 64 specifies the position of the region of interest in the radiation image acquired in step S10. In step S64, the movement amount derivation unit 64 derives the movement amount of the ultrasound unit 30 caused by the second drive mechanism 38 in accordance with the position of the region of interest in the radiation image specified in step S62. In step S66, the controller 66 performs the control of driving the second drive mechanism 38 in accordance with the movement amount of the ultrasound unit 30 derived in step S62, and terminates the second control process.

As described above, the console 50 according to the aspect of the present disclosure comprises the processor, and the processor acquires the radiation image of the breast 2 put into the compressed state by the compression member 40, specifies the position of the region of interest in the radiation image, and derives the movement amount of the ultrasound unit 30 caused by the second drive mechanism 38 in accordance with the position of the region of interest in the radiation image.

With the console 50, it is possible to perform the control of automatically moving the ultrasound unit 30 in accordance with the position of the region of interest included in the radiation image, and it is possible to support the ultrasound imaging.

Figure 19:
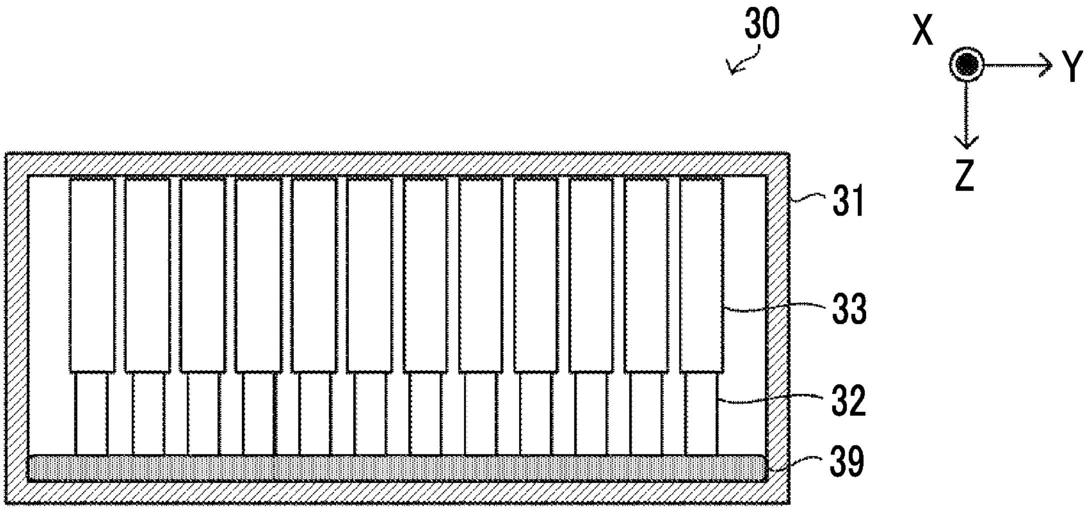
FIG. 19 is a view showing an example of another schematic configuration of the ultrasound unit.

In the embodiments described above, the form is described in which the scan mechanism 34 is provided in the ultrasound unit 30 and the ultrasound probe 32 is scanned by the scan mechanism 34, but the present disclosure is not limited to this. As shown in FIG. 19, the ultrasound unit 30 may include a plurality of ultrasound probes 32 arranged in a linear array or a matrix array in the case 31.

It should be noted that, in the embodiments described above, the form is described in which the console 50 is an example of a control apparatus according to the present disclosure, but an apparatus other than the console 50 may have the function of the control apparatus according to the present disclosure. In other words, an apparatus other than the console 50, such as the imaging apparatus 10 and the external apparatus, may have a part or all of the functions of the acquisition unit 60, the position specifying unit 62, the movement amount derivation unit 64, and the controller 66.

In the embodiments described above, for example, as hardware structures of processing units that execute various types of processes, such as the controller 20, the acquisition unit 60, the position specifying unit 62, the movement amount derivation unit 64, and the controller 66, various processors shown below can be used. As described above, in addition to the CPU that is a general-purpose processor that executes software (program) to function as various processing units, the various processors include a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured by using one of the various processors or may be configured by using a combination of two or more processors of the same type or different types (for example, a combination of a plurality of FPGAs or a combination of a CPU and an FPGA). Moreover, a plurality of processing units may be configured of one processor.

A first example of the configuration in which the plurality of processing units are configured by using one processor is a form in which one processor is configured by using a combination of one or more CPUs and the software and this processor functions as the plurality of processing units, as represented by computers, such as a client and a server. Second, as represented by a system on chip (SoC) or the like, there is a form in which the processor is used in which the functions of the entire system which includes the plurality of processing units are realized by a single integrated circuit (IC) chip. In this way, as the hardware structure, the various processing units are configured by using one or more of the various processors described above.

Further, the hardware structure of these various processors is, more specifically, an electric circuit (circuitry) in which circuit elements such as semiconductor elements are combined.

In addition, in each embodiment described above, the aspect is described in which the various programs in the imaging apparatus 10 are stored (installed) in the ROM included in the controller 20 in advance, and the control program 57 in the console 50 is stored in the storage unit 52 in advance, but the present disclosure is not limited to this. The various programs and the control program 57 in the imaging apparatus 10 may be provided in a form of being recorded in a recording medium, such as a compact disc read only memory (CD-ROM), a digital versatile disc read only memory (DVD-ROM), and a universal serial bus (USB) memory. In addition, a form may be adopted in which the various programs and the control program 57 in the imaging apparatus 10 are downloaded from an external apparatus via the network. Further, the technique of the present disclosure extends to a storage medium that non-transitorily stores a program in addition to the program.

In the technique of the present disclosure, the embodiments and the examples described above can be combined as appropriate. The above-described contents and the above-shown contents are detailed description for parts according to the technique of the present disclosure, and are merely examples of the technique of the present disclosure. For example, the above description related to the configuration, the function, the action, and the effect is the description related to the examples of the configuration, the function, the action, and the effect of the parts according to the technique of the present disclosure. As a result, it is needless to say that unnecessary parts may be deleted, new elements may be added, or replacements may be made with respect to the above-described contents and the above-shown contents within a range that does not deviate from the gist of the technique of the present disclosure.

What is claimed is:

1. An imaging system comprising:

an imaging apparatus including:

a compression member that is configured to put a breast into a compressed state between the compression member and an imaging table;

a radiation source that is configured to irradiate the breast put into the compressed state by the compression member with radiation;

an ultrasound unit that is configured to capture an ultrasound image of the breast put into the compressed state by the compression member, that is disposed on a side of an upper surface of the compression member opposite to a contact surface with the breast, and that has an in-plane position in a plane direction of the upper surface and a height from the upper surface, the in-plane position and the height being changeable;

a first sensor that is configured to detect the height of the ultrasound unit from the upper surface; and a second sensor that is configured to detect the in-plane position of the ultrasound unit, and a control apparatus including at least one processor, wherein the at least one processor is configured to:

acquire, in an order of time, height information indicating the height of the ultrasound unit from the upper surface;

make a determination whether or not the height indicated by the height information satisfies a predetermined condition;

specify, based on a result of the determination, a first position that is the in-plane position of the ultrasound unit in a predetermined period including a point in time at which the predetermined condition is satisfied;

acquire a radiation image of the breast put into the compressed state by the compression member;

associate first coordinates of the radiation image with the in-plane position;

specify the first coordinates of the radiation image corresponding to the specified first position;

perform control of displaying, on a display, a first marker indicating the specified first coordinates in a state of being superimposed on the radiation image;

specify, in a case in which it is determined that the height indicated by the height information does not satisfy the predetermined condition, a second position that is the in-plane position of the ultrasound unit in the predetermined period including a point in time at which the predetermined condition is not satisfied;

specify second coordinates of the radiation image corresponding to the specified second position; and perform control of displaying, on the display, a second marker that indicates the specified second coordinates, and that has at least one of a different color, a different line type, a different thickness, or a different shape from the first marker, in a state of being superimposed on the radiation image.

2. The imaging system according to claim 1, wherein the at least one processor is configured to perform control of storing the radiation image and the first coordinates in a storage unit in association with each other.

3. The imaging system according to claim 1, wherein the at least one processor is configured to determine whether or not the height satisfies the predetermined condition by determining whether or not a temporal change amount of the height of the ultrasound unit from the upper surface in the predetermined period is equal to or greater than a predetermined threshold value.

4. The imaging system according to claim 1, wherein the at least one processor determines whether or not the height satisfies the predetermined condition by determining whether or not an absolute value of the height of the ultrasound unit from the upper surface is smaller than a predetermined threshold value.

5. The imaging system according to claim 1, wherein the at least one processor specifies, in a case in which it is determined that the height indicated by the height information satisfies the predetermined condition, an angle of the ultrasound unit with respect to the upper surface in the predetermined period including the point in time at which the predetermined condition is satisfied, in addition to the first position.

6. The imaging system according to claim 1, wherein the imaging apparatus further includes:

a first drive device including a first drive source that moves the ultrasound unit between at least two states of an approach state in which the ultrasound unit approaches the upper surface, and a separation state in which the ultrasound unit is separated from the upper surface as compared to the approach state; and a second drive device including a second drive source that moves the ultrasound unit put into the separation state by the first drive device in the plane direction of the upper surface.

7. A control method comprising:

irradiating a breast in a compressed state between a compression member and an imaging table with radiation from a radiation source;

capturing, by an ultrasound unit, an ultrasound image of the breast put into the compressed state by the compression member, the ultrasound unit being disposed on a side of an upper surface of the compression member opposite to a contact surface with the breast, and that has an in-plane position in a plane direction of the upper surface and a height from the upper surface, which are the in-plane position and the height being changeable;

detecting the height of the ultrasound unit from the upper surface by a first sensor;

detecting the in-plane position of the ultrasound unit by a second sensor;

acquiring, in an order of time, height information indicating the height of the ultrasound unit from the upper surface;

making a first determination that the height indicated by the height information satisfies a predetermined condition;

specifying, in response to the first determination, a first position that is the in-plane position of the ultrasound unit in a predetermined period including a point in time at which the predetermined condition is satisfied;

acquiring a radiation image of the breast put into the compressed state by the compression member;

associating first coordinates of the radiation image with the in-plane position;

specifying the first coordinates of the radiation image corresponding to the specified first position;

performing control of displaying, on a display, a first marker indicating the specified first coordinates in a state of being superimposed on the radiation image;

making a second determination that the height indicated by the height information does not satisfy the predetermined condition;

specifying, in response to the second determination, a second position that is the in-plane position of the ultrasound unit in the predetermined period including a point in time at which the predetermined condition is not satisfied;

specifying second coordinates of the radiation image corresponding to the specified second position;

and performing control of displaying, on the display, a second marker that indicates the specified second coordinates, and that has at least one of a different color, a different line type, a different thickness, or a different shape from the first marker, in a state of being superimposed on the radiation image.

8. A non-transitory computer-readable storage medium storing a control program for causing a computer to execute a process comprising:

irradiating a breast in a compressed state between a compression member and an imaging table with radiation by a radiation source;

capturing, by an ultrasound unit, an ultrasound image of the breast put into the compressed state by the compression member, the ultrasound unit being disposed on a side of an upper surface of the compression member opposite to a contact surface with the breast, and that has an in-plane position in a plane direction of the upper surface and a height from the upper surface, the in-plane position and the height being changeable;

detecting the height of the ultrasound unit from the upper surface by a first sensor;

detecting detect the in-plane position of the ultrasound unit by a second sensor;

acquiring, in an order of time, height information indicating the height of the ultrasound unit from the upper surface;

making a determination whether or not the height indicated by the height information satisfies a predetermined condition;

specifying, based on a result of the determination, a first position that is the in-plane position of the ultrasound unit in a predetermined period including a point in time at which the predetermined condition is satisfied;

acquiring a radiation image of the breast put into the compressed state by the compression member;

associating first coordinates of the radiation image with the in-plane position;

specifying the first coordinates of the radiation image corresponding to the specified first position;

performing control of displaying, on a display, a first marker indicating the specified first coordinates in a state of being superimposed on the radiation image;

specifying, in a case in which it is determined that the height indicated by the height information does not satisfy the predetermined condition, a second position that is the in-plane position of the ultrasound unit in the predetermined period including a point in time at which the predetermined condition is not satisfied;

specifying second coordinates of the radiation image corresponding to the specified second position; and performing control of displaying, on the display, a second marker that indicates the specified second coordinates, and that has at least one of a different color, a different line type, a different thickness, or a different shape from the first marker, in a state of being superimposed on the radiation image.

* * * * *